(12) United States Patent
Board

(10) Patent No.: US 7,505,852 B2
(45) Date of Patent: Mar. 17, 2009

(54) PROBABILISTIC STRESS WAVE ANALYSIS SYSTEM AND METHOD

(75) Inventor: David B. Board, Boca Raton, FL (US)

(73) Assignee: Curtiss-Wright Flow Control Corporation, Falls Church, VA (US)

( * ) Notice: Subject to any disclaimer, the term of this patent is extended or adjusted under 35 U.S.C. 154(b) by 0 days.

(21) Appl. No.: 11/750,159

(22) Filed: May 17, 2007

(65) Prior Publication Data

US 2007/0282545 A1 Dec. 6, 2007

Related U.S. Application Data

(60) Provisional application No. 60/747,423, filed on May 17, 2006.

(51) Int. Cl.
*G06F 19/00* (2006.01)
*G06F 11/30* (2006.01)

(52) U.S. Cl. .......................... 702/33; 702/56; 702/179; 702/182

(58) Field of Classification Search .................. 702/33, 702/56, 179, 182, 183, 185; 73/570, 587
See application file for complete search history.

(56) References Cited

U.S. PATENT DOCUMENTS

| 3,554,012 A | 1/1971 | Schoel |
| 3,842,663 A | 10/1974 | Harting et al. |
| 4,530,240 A | 7/1985 | Board et al. |
| 5,251,151 A * | 10/1993 | Demjanenko et al. ......... 702/56 |
| 5,852,793 A * | 12/1998 | Board et al. .................. 702/56 |
| 6,351,713 B1 | 2/2002 | Board et al. |
| 6,499,350 B1 | 12/2002 | Board et al. |
| 6,553,839 B2 | 4/2003 | Board |
| 6,679,119 B2 | 1/2004 | Board |
| 6,684,700 B1 | 2/2004 | Board |

FOREIGN PATENT DOCUMENTS

GB 2282297 A 3/1995

\* cited by examiner

*Primary Examiner*—Bryan Bui
(74) *Attorney, Agent, or Firm*—Pearne & Gordon LLP

(57) ABSTRACT

A statistical process, and system for implementing the process, is described for the analysis of stress waves generated in operating machinery or equipment. This technique is called Probabilistic Stress Wave Analysis. The process is applied to a population of individual "feature" values extracted from a digitized time waveform (such as a 2 second Stress Wave Pulse Train, or a 2 month history of Stress Wave Energy). Certain numeric descriptors of the statistical distributions of computed features are then employed as inputs to decision making routines (such as neural networks or simple threshold testing) to accurately classify the condition represented by the original time waveform data, and thereby determine a status of the operating machine/equipment.

35 Claims, 15 Drawing Sheets

PROBABILISTIC STRESS WAVE ANALYSIS SYSTEM AND METHOD

CROSS-REFERENCES TO RELATED APPLICATIONS

This application claims the benefit of provisional application Ser. No. 60/747,423 filed on May 17, 2006, and incorporated herein by reference.

BACKGROUND OF THE INVENTION

The present invention relates generally to analytical techniques for diagnosing machine conditions, and more particularly to the use of advanced stress wave analysis techniques to detect discrepant conditions in operating machinery.

Stress Wave Analysis (SWAN) is an ultrasonic technique for the real time, in-situ, measurement of friction and shock. The use of "stress waves" and their analysis is the topic of a number of patents, which will be briefly described hereinbelow:

U.S. Pat. No. 4,530,240, titled "Method and Apparatus for Diagnosing Machine Condition, and which is incorporated herein by reference, teaches a means for predicting machine failure by monitoring stress waves produced by friction and shock events.

U.S. Pat. No. 5,852,793, titled: METHOD AND APPARATUS FOR PREDICTIVE DIAGNOSIS OF MOVING MACHINE PARTS, and incorporated herein by reference, describes Stress Wave Analysis (SWAN) technology resulting from more than a decade of research and development activity. The technology includes analog and digital hardware designs, as well as software, that significantly increase signal to noise ratio, implement SWAN technology in low cost PC based platforms, and provide data logging and predictive maintenance capability. The disclosed method includes new ways of displaying SWAN data for simplified analysis, as well as Time Domain Feature Extraction software that provides "intelligent data compression" for use with Artificial Intelligence software.

U.S. Pat. No. 6,351,713, titled: DISTRIBUTED STRESS WAVE ANALYSIS SYSTEM, and incorporated herein by reference, discloses a next generation of SWAN products, which combine Stress Wave Analysis with Artificial Intelligence to provide automation to the interpretation of SWAN data. This improvement provides a further reduction in the skill levels and training required to use SWAN technology for accurate predictive maintenance, and extends SWAN capabilities for fault location/isolation and remaining useful life projection. A Frequency Domain Feature Extraction method and a proprietary Data Fusion Architecture are disclosed for providing very accurate fault detection, with very low probability of false alarms. The hardware designs described in this patent provide additional improvement of signal to noise ratio, while significantly reducing the size, weight, and power consumption of SWAN hardware, so that it becomes more practical for a variety of mobile and fixed base applications.

U.S. Pat. No. 6,499,350 titled: FOREIGN OBJECT DETECTION (FOD), and incorporated herein by reference, teaches the use of a specialized hardware implementation of SWAN technology for application to turbo machinery, which can be seriously damaged by the ingestion of foreign objects. The disclosed design is applicable for airborne, marine, and ground based applications.

U.S. Pat. No. 6,684,700 titled: STRESS WAVE SENSOR, incorporated herein by reference, defines functional performance requirements for a sensor specifically designed to detect stress waves. This reference also defines the quantitative relationships between the sensor specifications and the analog signal conditioning that is used to filter, amplify, and demodulate the sensor's broad band output.

U.S. Pat. No. 6,553,839 titled: METHOD FOR STIMULATING A SENSOR AND MEASURING THE SENSOR'S OUTPUT OVER A FREQUENCY RANGE and incorporated by reference, describes a calibration technique tailored to the peculiar functional specifications of certain stress wave sensors.

U.S. Pat. No. 6,679,119 titled: MULTI-FUNCTION SENSOR, and incorporated herein by reference, teaches that, for many predictive maintenance applications, SWAN and vibration analysis are complimentary technologies. The sensor described in this patent provides electrical signals proportional to both vibration and stress waves from a single device. This multi-function sensor significantly reduces cost, weight and power requirements compared to separate sensors. This device is applicable for both airborne and industrial applications.

SWAN techniques, some of which are discussed on some of the above cited references, typically employ a specialized, externally mounted ultrasonic sensor along with unique signal conditioning to produce a Stress Wave Pulse Train (SWPT) time waveform. This SWPT is then digitized and analyzed to determine the "health" of the operating machine. Because friction is also a function of operational parameters, such as load and speed of the monitored machine, the analysis process should take these normal variables into account, to prevent false or premature indication of a discrepant condition. This has been accomplished by analyzing short (1-10 second) "snapshots" of data, taken at reference operating conditions.

However, the prior art techniques have suffered from a number of drawbacks, including a requirement that similar operating conditions be imposed to data "snapshots" in order to have an "apples-to-apples" comparison situation. Such a requirement is often impractical because it may be difficult, or impossible, to impose such uniformity in operating conditions. A way around such limitations in the SWAN process would be useful.

SUMMARY OF THE INVENTION

Provided are a plurality of embodiments of the invention, including, but not limited to, a method for determining a current status of an apparatus, the method comprising the steps of:

monitoring stress waves generated by the apparatus during a normal operation of the apparatus for at least one time period to generate first stress wave data;

analyzing at least a portion of the first stress wave data to generate first analyzed data that captures one or more features of the first stress wave data;

processing at least a portion of the first analyzed data to generate baseline data, wherein the baseline data has substantially reduced influence from normal operating variations compared to the first analyzed data;

further monitoring stress waves generated by the apparatus during a current operation of the apparatus for a current time period to generate second stress wave data;

analyzing at least a portion of the second stress wave data to generate second analyzed data that captures one or more features of the second stress wave data;

processing at least a portion of the second analyzed data to generate current status data, wherein the current status data also has substantially reduced influence from normal operating variations compared to the second analyzed data; and comparing the current status data to the baseline data to determine the current status of the apparatus.

Also provided is the above method wherein the baseline data includes baseline probabilistic data representing a normal operating condition of the apparatus, and wherein the current status data includes current probabilistic data representing a current operating condition, and further wherein the comparing step compares the baseline probabilistic data to the current probabilistic data to determine the current status of the apparatus.

Still further provided is the above method wherein both of the probabilistic data include the results of one or more of: a third moment test for a normal distribution, a maximum value of the population, a ratio of (the maximum−the mean) divided by (the maximum−the minimum), a ratio of the standard deviation of the population to the mean of the population, a skewness coefficient, and the kurtosis of the population.

Alternatively provided is the method for determining a current status of an apparatus described above, where the first stress wave data includes data obtained from a first location of the apparatus, and also includes data obtained from a second location of the apparatus different from the first location, and where the second stress wave data includes data obtained from the first location of the apparatus, and also includes data obtained from the second location of the apparatus, such that the baseline data is derived from a difference between the portion of the first analyzed data obtained from the first location and the portion of the first analyzed data obtained from the second location, and further such that the current status data is derived from a difference between the portion of the second analyzed data obtained from the first location and the portion of the second analyzed data obtained from the second location.

Further provided is a method for determining a current status of an apparatus, the method comprising the steps of:
monitoring stress waves generated by the apparatus during a current operation of the apparatus for a current time period to generate current stress wave data;
analyzing at least a portion of the current stress wave data to generate current analyzed data that captures one or more features of the current stress wave data;
processing at least a portion of the current analyzed data to generate probabilistic current status data, wherein the probabilistic current status data has substantially reduced influence from normal operating variations compared to the current analyzed data; and
comparing the probabilistic current status data to probabilistic baseline data to determine the current status of the apparatus.

In addition is provided a method for determining a current status of an apparatus, the method comprising the steps of:
monitoring stress waves generated by the apparatus at a first location during a current operation of the apparatus for a current time period to generate first current stress wave data;
analyzing at least a portion of the first current stress wave data to generate first current analyzed data that captures one or more features of the first current stress wave data;
monitoring stress waves generated by the apparatus at a second location different than the first location during the current operation of the apparatus for the current time period to generate second current stress wave data;
analyzing at least a portion of the second current stress wave data to generate second current analyzed data that captures one or more features of the current second stress wave data;
processing at least a portion of the first current analyzed data and the second current analyzed data to generate current status data based on a difference between the first current analyzed data and the second current analyzed data; and
comparing the current status data to a threshold to determine the current status of the apparatus.

Further provided is the above method wherein the threshold includes baseline PDF descriptors, and wherein the current status data includes current PDF descriptors such that the comparing includes comparing the current PDF descriptors to said baseline PDF descriptors In addition, a system is provided for determining a current status of an apparatus, the system comprising: at least one sensor mounted on or in the apparatus for monitoring stress waves generated by the apparatus during a normal operation of the apparatus for at least one time period to generate first stress wave data; a feature extraction device adapted for analyzing at least a portion of the first stress wave data to generate first analyzed data that captures one or more features of the first stress wave data; means for processing at least a portion of the first analyzed data to generate baseline data, wherein the baseline data has substantially reduced influence from normal operating variations compared to the first analyzed data; means for further monitoring stress waves generated by the apparatus during a current operation of the apparatus for a current time period to generate second stress wave data; means for analyzing at least a portion of the second stress wave data to generate second analyzed data that captures one or more features of the second stress wave data; means for processing at least a portion of the second analyzed data to generate current status data, wherein the current status data also has substantially reduced influence from normal operating variations compared to the second analyzed data; and means comparing the current status data to the baseline data to determine the current status of the apparatus.

Further provided is system for determining a current status of an apparatus, the system comprising: a sensor mounted on or in the apparatus for monitoring stress waves generated by the apparatus during a current operation of the apparatus for a current time period to generate current stress wave data; means for analyzing at least a portion of the current stress wave data to generate current analyzed data that captures one or more features of the current stress wave data; means for processing at least a portion of the current analyzed data to generate probabilistic current status data, wherein the probabilistic current status data has substantially reduced influence from normal operating variations compared to the current analyzed data; and means for comparing the probabilistic current status data to probabilistic baseline data to determine the current status of the apparatus.

Also provided is system for determining a current status of an apparatus, the system comprising: a first sensor mounted on or in the apparatus at a first location for monitoring stress waves generated by the apparatus during a current operation of the apparatus for a current time period to generate first current stress wave data; means for analyzing at least a portion of the first current stress wave data to generate first current analyzed data that captures one or more features of the first current stress wave data; a second sensor mounted on or in the apparatus at a second location different than the first location for monitoring stress waves generated by the apparatus during the current operation of the apparatus for the current time period to generate second current stress wave data; means for analyzing at least a portion of the second current stress wave data to generate second current analyzed data that captures one or more features of the current second stress wave data; means for processing at least a portion of the first current analyzed data and the second current analyzed data to generate current status data based on a difference between the first current analyzed data and the second current analyzed data; and means for comparing the current status data to a threshold to determine the current status of the apparatus.

Some examples of the means for implementing the above systems are disclosed herein and additional means for implementing the system are disclosed in the patent references that are incorporated by reference.

Also provided are additional embodiments of the invention, some, but not all of which, are described hereinbelow in more detail.

BRIEF DESCRIPTION OF THE DRAWINGS

The features and advantages of the examples of the present invention described herein will become apparent to those skilled in the art to which the present invention relates upon reading the following description, with reference to the accompanying drawings, in which.

DETAILED DESCRIPTION OF THE EXAMPLE EMBODIMENTS

Figure 1:
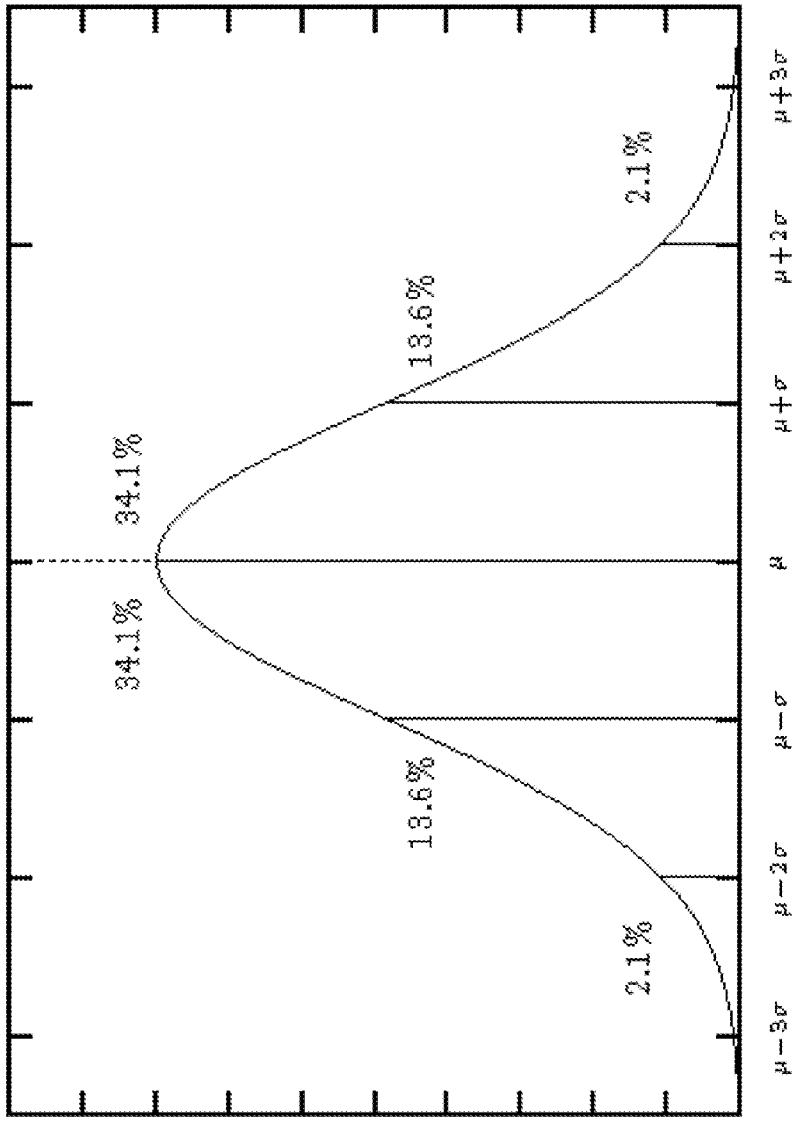
FIG. 1 is a diagrammatic representation of an example Gaussian Distribution of a Probability Density Function (PDF)

The statistical approach described herein can utilize data over the full operating regime of the machine, and, in addition to short "snapshots" of various operating periods of the machine, is used to analyze the long term historical "trend" data acquired over periods of hours, days, weeks and months. This approach is easily automated, and improves both the diagnostic and prognostic accuracy of a SWAN based machinery condition monitoring system.

The improved method provides a means of smoothing out operating characteristics of machines to compare current operating conditions to previous operating conditions, where the machine operation was considered to be optimal, or at least acceptable. This can be done by at least two different methods, both related in that they attempt to filter out the variations in SWAN data to allow monitoring during operation of the machine without any requirement of special operating modes or artificial scenarios.

Rather than merely comparing snapshots of SWAN data to one-another while attempting to provide similar operating conditions in the machine to make the results relevant to each other, one solution is to collect SWAN data over time (e.g., via snapshots in time, monitoring various time periods, or continuous monitoring, for example) and analyzing probabilistically that data so that trends in the data can be compared. The probabilistic analysis of stress waves (PSWAN) helps to smooth out the operating changes (including noise, random events, and operating variations), so that those differences are instead "averaged out", providing a trend that can give an accurate reflection of the current operating status, as compared to earlier operating statuses.

Another solution is to evaluate the difference of stress waves between two sensors mounted on different locations of the machine, rather than merely looking at snapshots of a single sensor. This allows the "common mode" noise and other variations common to the sensor to be subtracted out. This difference can then be used to evaluate operating status, where a large change in this "delta" gives an indication that a problem (or other change) is occurring within the monitored device.

Finally, the "delta" function can also be trended, if desired, by analyzing the delta data probabilistically.

Accordingly, two new classes of features have been developed to: 1) minimize the effects of speed and load in the data, and 2) to provide an indication of the status of equipment, such as the remaining useful life of the equipment. As discussed above, one of these new feature classes is based upon the difference between a computed feature value at two different sensor locations. The resulting "delta function" multi-sensor feature can be an effective means of eliminating the effects of load and speed from the SWAN data, resulting in a useful "delta feature". Another new class of features, the CUM (cumulative) function, can be employed to estimate "Life Used" or the probability of operating to a specified point, such as a warrantee period, without a failure. It can also be used, along with SWE level and rate of change, for making a Remaining Useful Life Estimate (RULE).

Time Domain Feature Extraction software was originally developed for application to Digital Record (DR) "snapshots" of the Stress Wave Pulse Train (SWPT). However, this same software can be employed for Trend Domain Feature Extraction (TDFE) as disclosed herein. Trend Domain Feature Extraction software can provide statistical characterization of trended stress wave features (SWE, SWPA, etc.). For Trend Domain Feature Extraction, the TDFE software will utilize various "snapshots" to analyze for trends. For example, the TDFE can utilize the last 100 "snapshot feature" values that are stored in the data base from each sensor location. The Snapshot and Trend features can then be used as inputs to neural networks, which are embedded within a Data Fusion Architecture (DFA). The output of the DFA is knowledge about the operational status and health of the monitored machine.

Feature Extraction provides a computational technique for the intelligent compression of large files of time waveform data (raw stress wave data) into a small set of numeric values that accurately characterize the time waveform data in, for example, the time and frequency domains by analyzing the waveform data to extract desired features to produce analyzed data. For example, friction features computed from the SWPT are the end results of a complex system of mechanical elements, fluid dynamics, operating speeds, and dynamic loading. Under stress, such complex systems exhibit early changes in system behavior and condition, including changes in the Probability Density Function (statistical distribution) of measured stress wave features, particularly in the ±3 sigma range. Statistical measures of the Probability Density Function (PDF) of trended stress wave features, over a range of operating conditions, can therefore be used to detect changes to system stress/health.

Time/Trend Domain Feature extraction software (which might utilize Time Domain Feature Extraction software such as described in the cited prior art) can be used for processing the analyzed data (e.g., features of interest) for generating data including a set of "Trend Features" including statistical descriptors of Trend Feature values useful in classifying the operating stresses, condition, and "health" of operating machinery. The Trend Features, including statistical descriptors of Trend Feature values, can be employed by decision making software, such as neural networks, or in rule based logic, in a suitably configured Data Fusion Architecture (DFA) to classify and evaluate machine operating conditions.

For any given mechanical condition of a machine, SWE values can vary over a fixed range between minimum and maximum values (i.e., the Range of Variability (ROV)). The uncertainty as to where, within the ROV, any individual SWE reading will fall is a function of Hidden Variables. Hidden Variables can include (but are not limited to): dynamic loads of unknown frequency and amplitude; fluid contamination of the lubricant; particulate contamination of the lubricant; degradation of the lubricant additive package; fatigue life status of damage zone materials during a failure process; and micro contact/fluid dynamics within the damage zone during a failure process. Complex interactions between hidden variables further randomize the probability of obtaining any given SWE reading, within the ROV. Hidden variables typically cannot be defined analytically, but can be addressed statistically.

During normal operation of healthy machinery with efficient lubrication, the cumulative effects of hidden variables on SWE or SWPA values tend to be randomly distributed. The Probability Density Function (PDF) that typically best describes the randomly distributed measurements within the Range of Variability (ROV) is the Gaussian distribution, as shown in the example plot of FIG. 1. The Gaussian distribution is, by its nature, inherently symmetrical; i.e. for a statistically significant number of measurements, there will be as many measurements below the mean value as there are above the mean value. The Gaussian distribution also implies that 99.6% of the measurements will fall with the ROV from the mean minus 3 standard deviations ($\mu-3\sigma$) to the mean plus 3 standard deviations ($\mu+3\sigma$). As a mechanical fault or lubrication problem develops and progresses, this Gaussian PDF will change by becoming "skewed". The amount and type of skewness will change as a function of damage progression.

Figure 2:
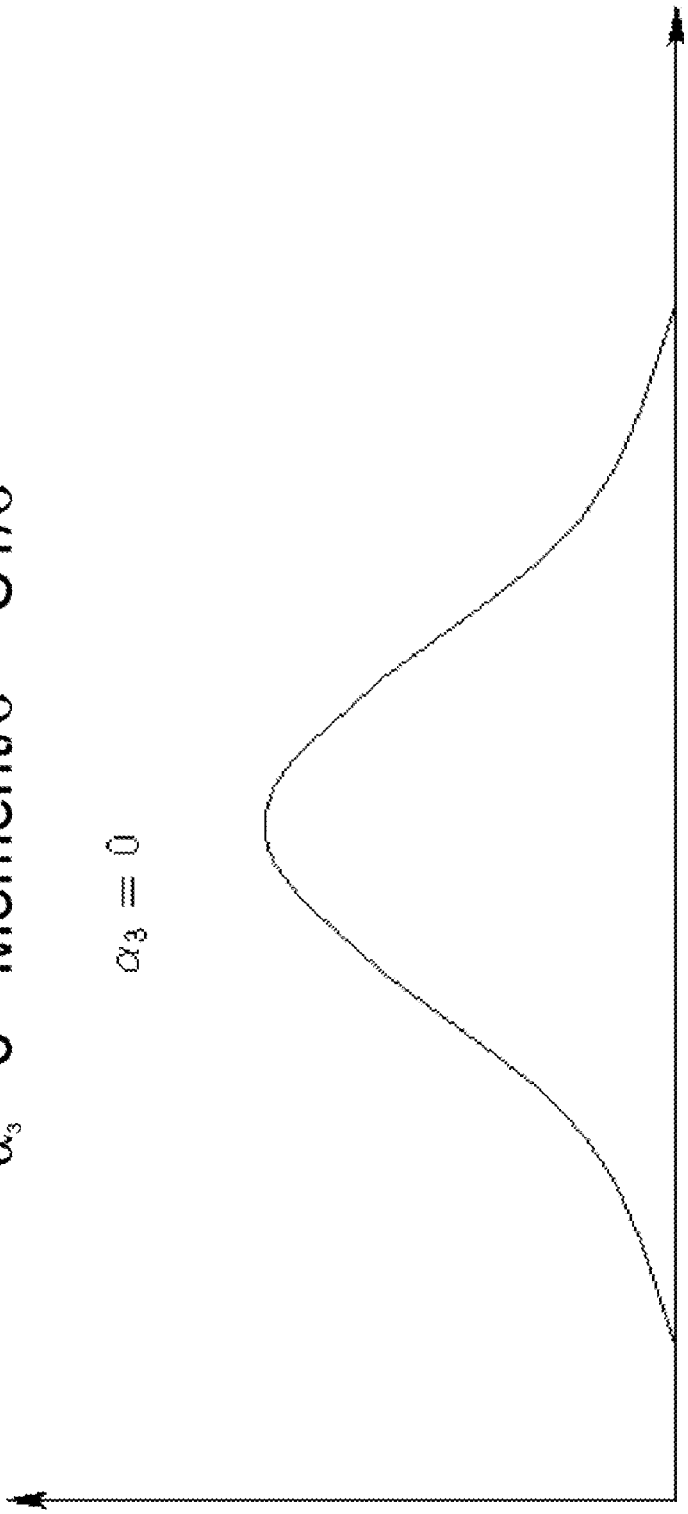
FIG. 2 is an example graphical representation of a PDF showing a skewness close to zero ($\alpha_3 \approx 0$)

FIG. 2 shows a normal curve with a skewness of zero. The Skewness Coefficient describes the nature and degree of asymmetry of the PDF, for a population of "Feature" values. Thus, for a "healthy" machine with adequate lubrication, operating within a normal range of speed/load conditions, the skewness is very close to 0 ($\alpha_3 \approx 0$), and thus would appear as shown in this figure.

Figure 3:
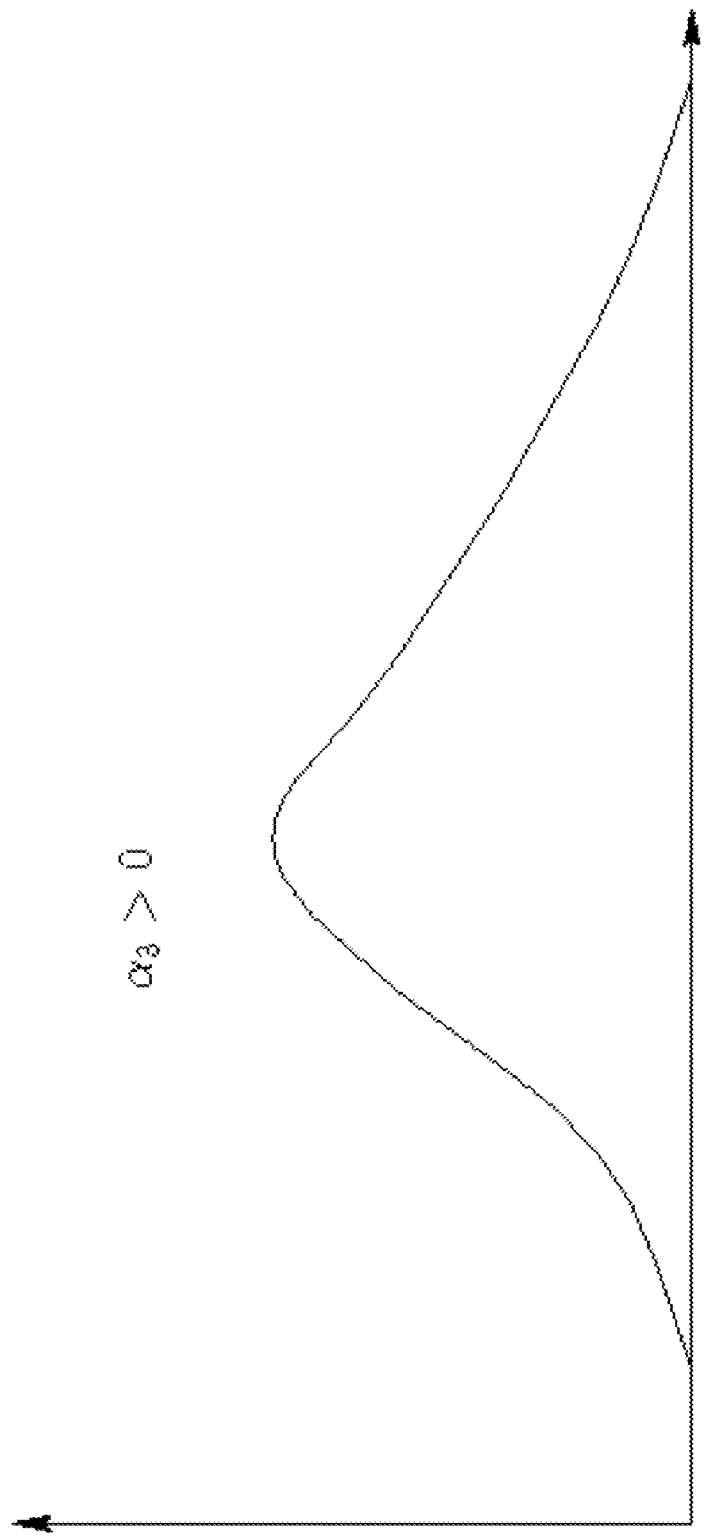
FIG. 3 is an example graphical representation of a positively skewed PDF ($\alpha_3 > 0$)

FIG. 3 shows an example distribution that is positively skewed. In the early stages of the failure process, for example in a component like a rolling element bearing, a Feature like SWE will eventually begin to have a small, but increased number, of higher values. This will cause the PDF to become positively skewed (as shown in FIG. 3) with a Skewness Coefficient that is greater than zero ($\alpha_3 > 0$)

Figure 4:
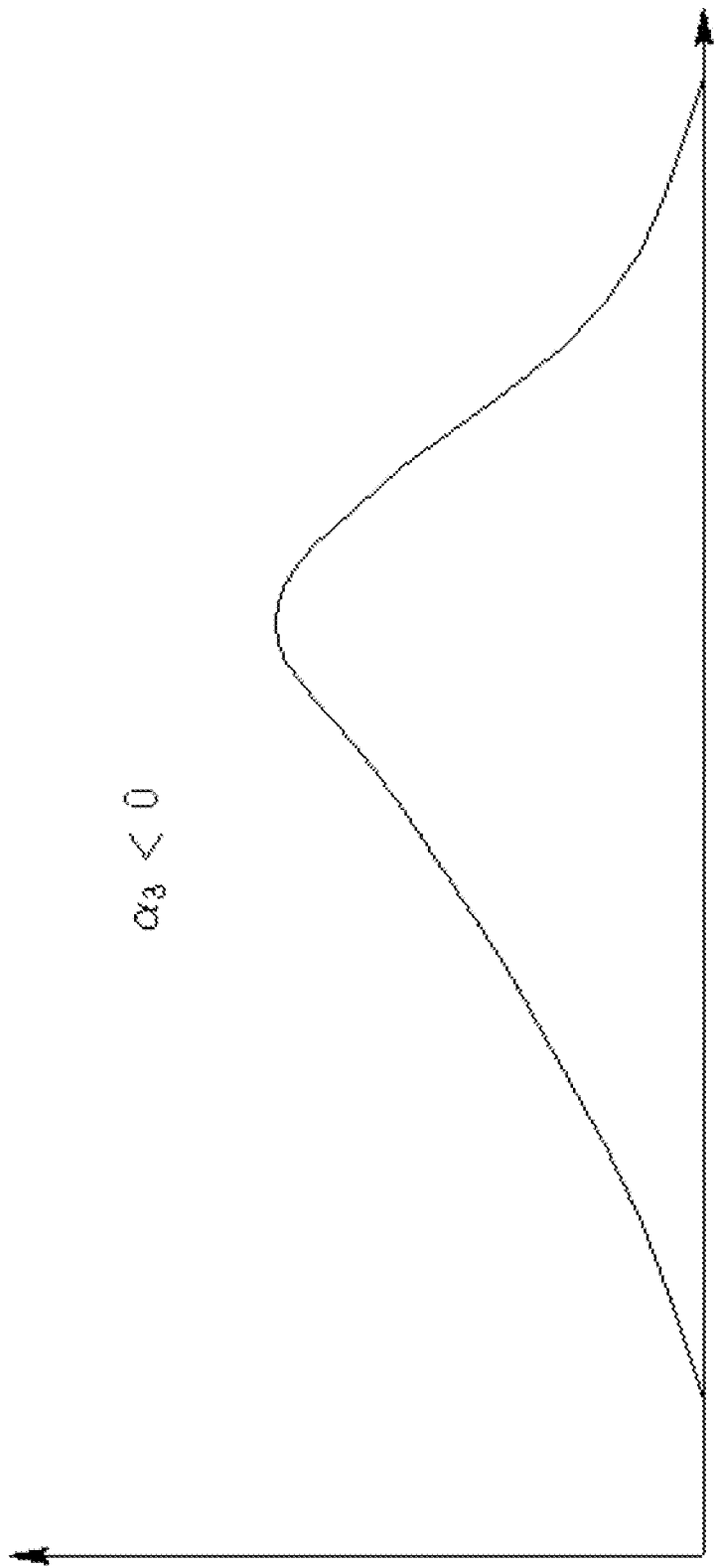
FIG. 4 is an example graphical representation of a negatively skewed PDF ($\alpha_3 < 0$)

FIG. 4 shows an example distribution that is negatively skewed. In the later stages of the failure process, a Feature like SWE will eventually have more and more high values. This will cause the mean and median value of SWE to increase (shift to the right), and thus the PDF will become negatively skewed (as shown in FIG. 4) with a Skewness Coefficient less than 0 ($\alpha_3 < 0$).

Figure 5:
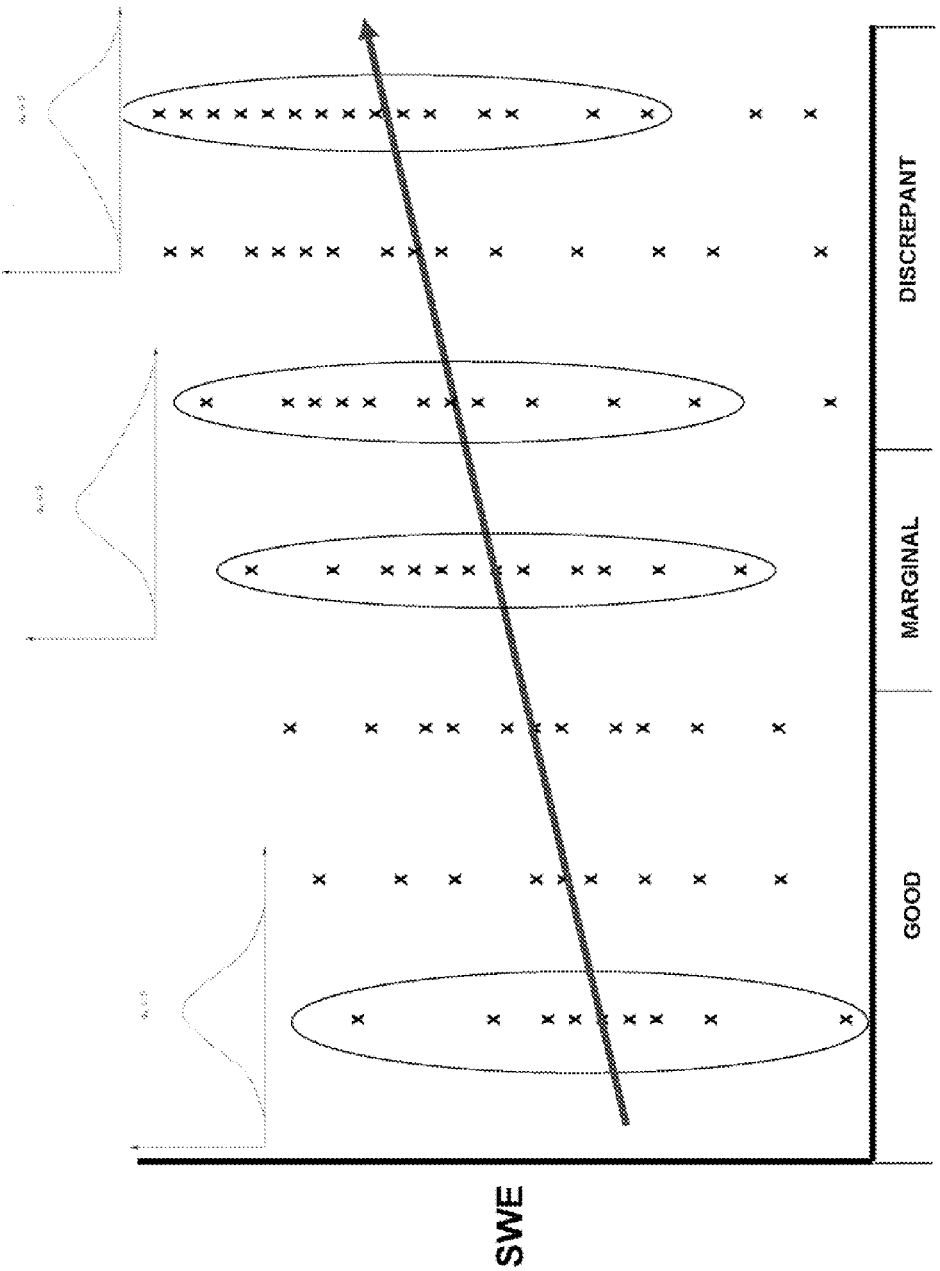
FIG. 5 illustrates an example Fault Progression with Changing PDF showing the associated impact on skewness.
Figure 6:
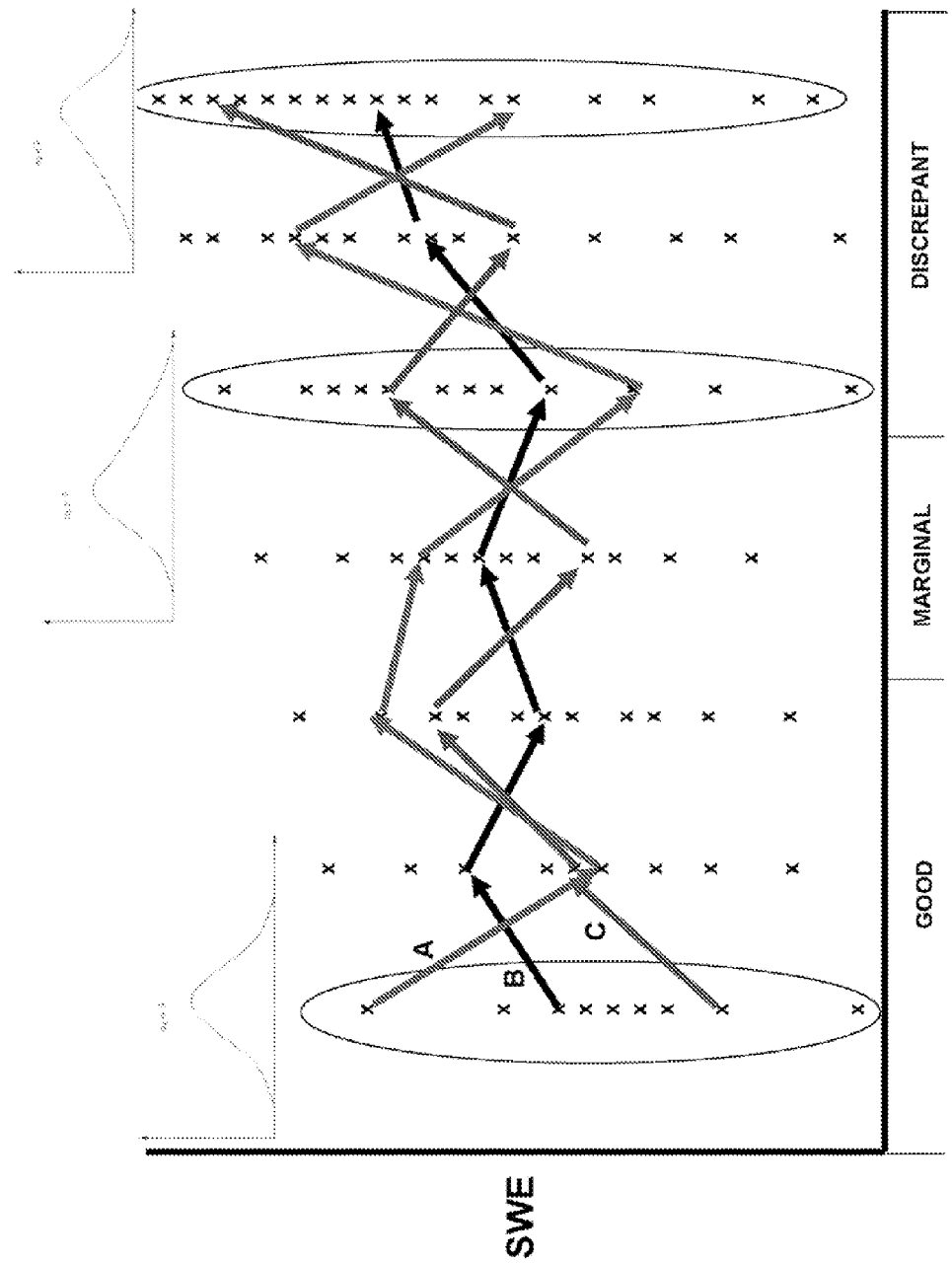
FIG. 6 illustrates an example of three possible Stress Wave Energy (SWE) histories during Fault Progression of the example of FIG. 5.

Single point measurement histories, from the same set of historical PDF's, can appear quite different, and (in the short term) even misleading. FIGS. 5 and 6 show a spread of points collected at various times. Each vertical collection of points is a collection of data points taken at different times, but for the same general time period (i.e., machine condition), with the vertical axes representing a magnitude of the data value. Moving right, each next vertical collection of points is a collection of points (a machine condition) taken at a later time period. Thus, the progression sequence is from left to right. Note that the early collections of points (at the left), appear relatively randomly distributed in a normal fashion, but as one moves to the right, this randomness becomes skewed (i.e., less "normal"), as shown in FIG. 6, first skewing positively, and then skewing negatively as the average value begins to increase.

Single point measurements typically do not provide a "complete picture" of the situation at any point in time because variations caused by operating conditions, noise, etc. can randomly distribute various values, causing the vertical spread of values shown in the plots of FIGS. 5 and 6. A PDF can be characterized by calculation of statistical descriptors (such as mean, standard deviation, 3rd moment, skewness coefficient, kurtosis, etc.) from the last "n" readings. The number "n" must be statistically significant, but should not cover more elapsed time than about 5%-10% percent of the Failure Progression Interval (FPI) (The FPI is the elapsed time between reliable detection of a problem, and the end of useful life of the monitored machine). (Statistically significant, for example, means at least one "mission cycle" for variable speed/load machines.)

Because SWAN measurements are sensitive to the earliest stages of damage, and most failure modes have an FPI of several hundred hours, "n" measurements must be typically obtained in about 10 to 100 hours. If measurements are made at about 5 minute intervals, for example, PDF descriptors can be continuously updated based upon the last 100 measurements, covering about 8.3 hours of operation.

Specialized Feature Extraction (FE) software has been developed for the purpose of accurately characterizing the Stress Wave Pulse Train (SWPT) and intelligently compressing the (SWPT) Digital Record (DR) files. This FE software can be employed to characterize historical trends of time domain features computed from DR's. Although this custom SWAN Feature Extraction software is tailored to the interpretation of the SWPT for the quantitative analysis of friction and shock events in operating machinery, it can be applied to any type of time waveform or historical trended data, if desired.

Figure 7:
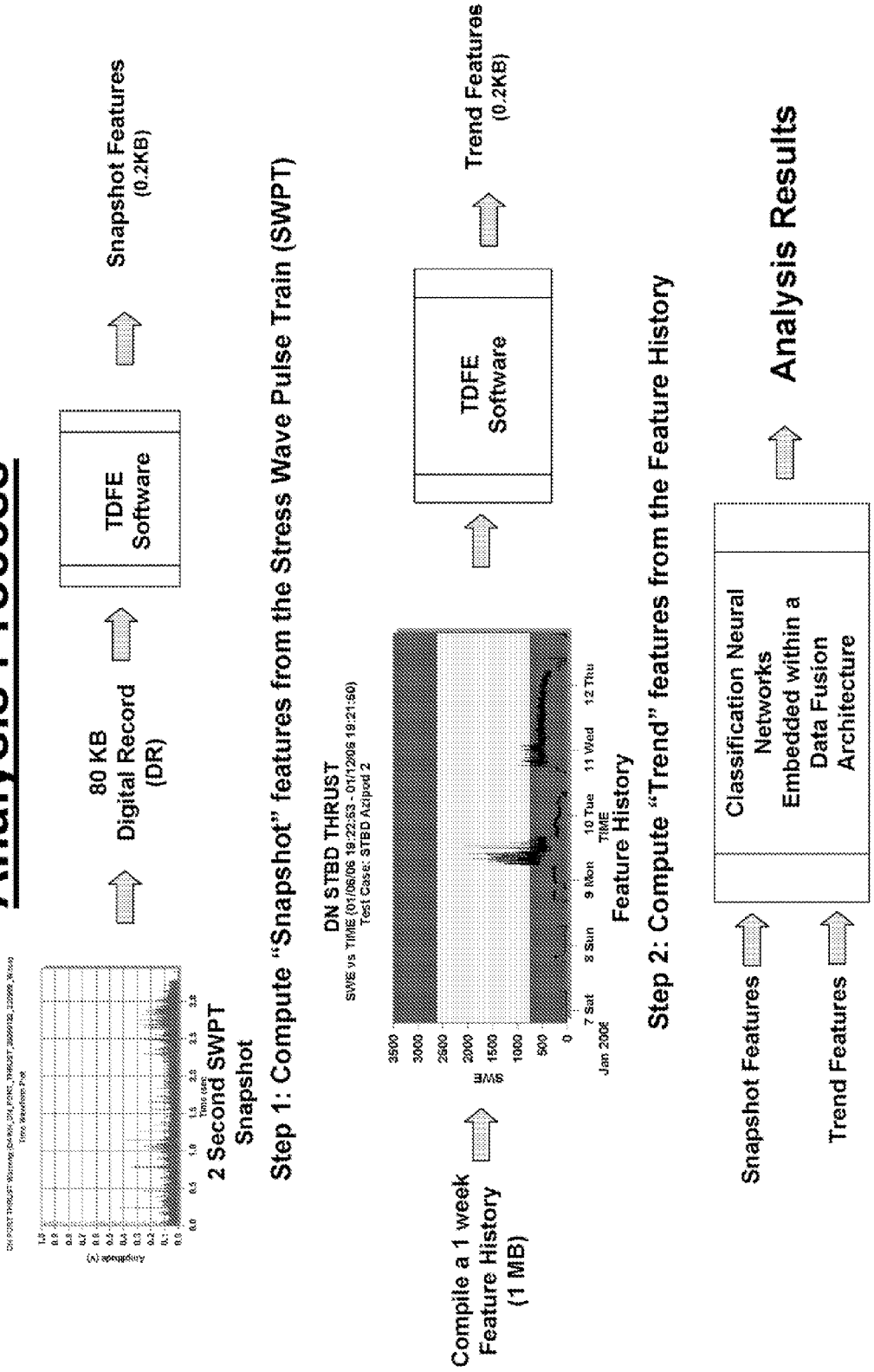
FIG. 7 represents a block diagram flow chart for an example Probabilistic Process for detecting impending faults/failures.

The Time Domain Feature Extraction (TDFE) software (running on a processor) starts with the DR file of the SWPT, which is a short collection of the stress wave data (typically the amplitudes of the stress waves are recorded). Mathematical transforms are then applied to the time series data by the software for characterization of waveform features such as pulse amplitude, duration and energy content. FIG. 7 shows the analysis process. The SAME Time Domain Feature Extraction software can be adapted for use to compute "Snapshot" Features from 2 second DR's; as well as to compute "Trend" Features from sets of historical data, that are hours or days long.

Figure 8:
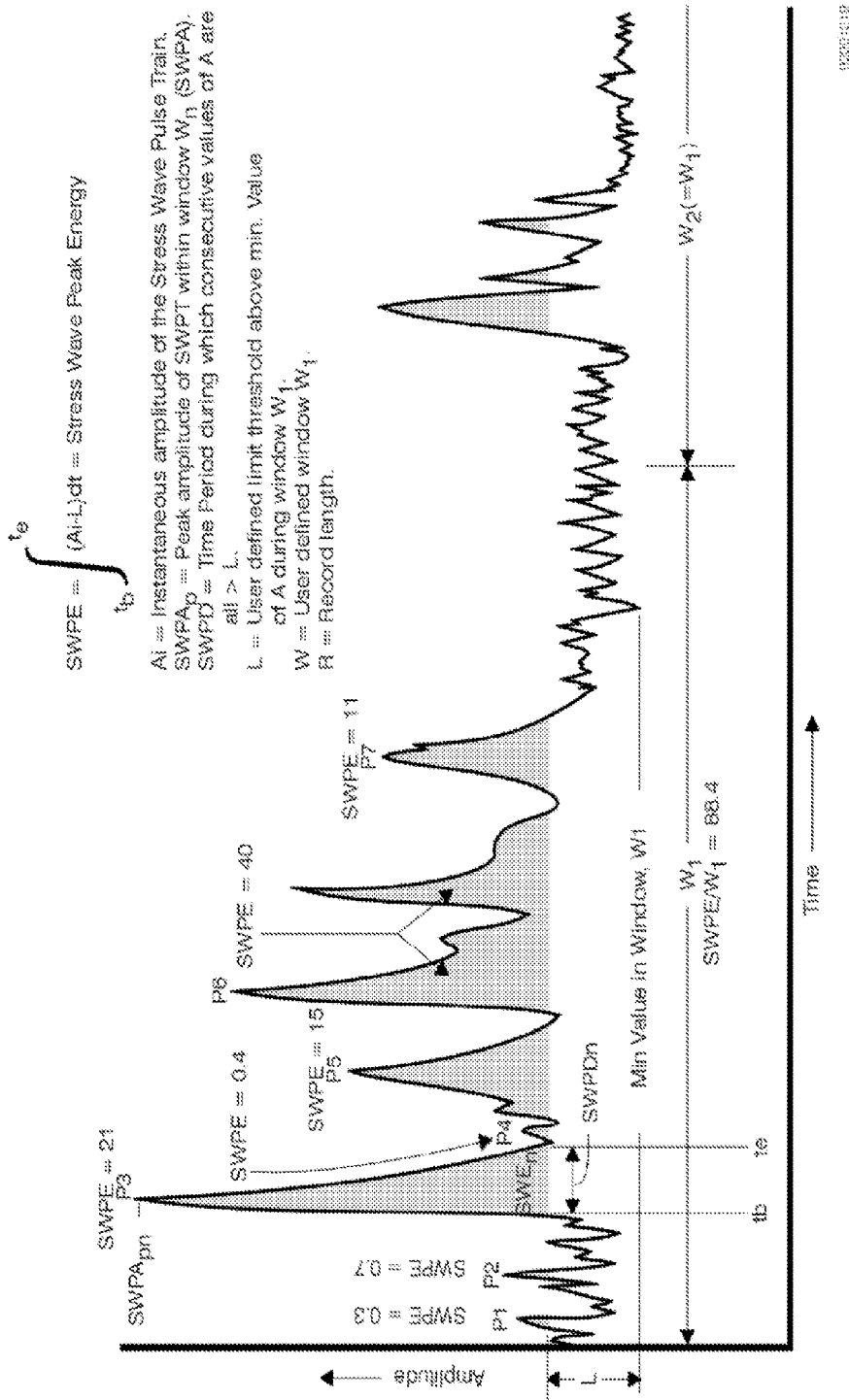
FIG. 8 is a graphical representation of an example Stress Wave Pulse Train Time Waveform.

FIG. 8 pictorially represents an example of a portion of the data of a SWPT time waveform (DR) file. The size of example SWPT DR files, when taken at the 20 k-sample rate for a duration of 2 seconds, is about 80 kB, written in binary format. The Time Domain Feature Extraction algorithms compress this data, and for the example into only 76 waveform features. Thus, the TDFE process converts 80 kB of data into less than 200 bytes of information, which can then be used by neural network algorithms to make informed decisions.

FIG. 8 illustrates how these extracted Time Domain Features of the SWPT (or a History time waveform) are calculated. This figure shows about 1.5 windows of duration "W". A Window is a user-defined number of time intervals (milliseconds, hours, days, etc.) typically selected as the period corresponding to a characteristic machine frequency, or a mission duration for History data. The length of W is constant for the full data record, and can be set by the analyst. A Record is a maximum of 200,000 data points (10 seconds of data at a 20,000 sample/sec rate). The data record length "R" is the total time duration represented by the data file.

All but two of the features extracted from the SWPT depend upon exceeding the limit threshold "L". This limit is calculated for each window as a multiple of the mean of the lowest 10% of positive values of the instantaneous amplitude "Ai" of the SWPT during the window. The Limit Threshold Factor (LTF) for computing L is constant for the full record length and can be set by the analyst. The limit threshold "L" is used to search for peaks, by measuring the time when the data point first exceeds L (the start of the peak event) and the time when a data point subsequently drops below L (the end of the peak event). A standard set of features are then computed for each peak event in the record. These features can include one or more of the following:

Stress Wave Peak Duration (SWPD)—The period of time between an upward a breech of the threshold L and when the Ai next falls below L;

Stress Wave Peak Amplitude (SWPA)—The maximum value of Ai during the SWPD; and

Stress Wave Peak Energy (SWPE)—The sum of (Ai-L) for each data point during the SWPD.

Similarly, a standard set of features can be calculated for each Window in the Record, which include one or more of:

Stress Wave Peak Energy per Window (SWPE/W)—The sum of all the individual SWPE values within a window;

Stress Wave Energy per Window (SWE/W)—The numeric sum of all the Ai values (greater than zero) for data points that occur during a window;

Peaks per Window (PEAKS/W)—The total number of SWPT peaks that occur during a window; and Peak Energy Factor per Window (PEF/W)—The ratio of the SWPE/W to the SWE/W.

There are also a standard set of features for the entire record, which include one or more of:

Stress Wave Energy per Record (SWE/R).—The numeric sum of all the Ai values greater than zero for all data points that occur during all windows of a data record;

Stress Wave Peak Energy per Record (SWPE/R)—The sum of all the individual SWPE values within a record;

Peak Energy Factor per Record (PEF/R)—The ratio of the SWPE/R to the SWE/R;

Peaks per Record (PEAKS/R)—The total number of SWPT peaks that occur during a record; and Stress Wave Peak Amplitude per Record (SWPA/R)—The maximum Ai value during the record.

A number of statistical parameters can be calculated. For example, six useful Statistical Parameters (S1, S2, S3, S4, S5 and S6) can be calculated a) for all the peaks in the record, and b) for each of the Window Length features, for the full record. This yields 76 time domain statistical parameters of the SWPT (refer to Table 1). The six Statistical Parameters (S1 through S6) are defined as follows:

S1: The $3^{rd}$ Moment test for Normal Distribution;

S2: The Maximum value of the population;

S3: The ratio of (Maximum−Mean)/(Maximum−Minimum);

S4: The Ratio of the standard deviation of the population to the mean of the population;

S5: The Skewness Coefficient: This is the ratio of S1 divided by the standard deviation; and S6: The Kurtosis of the population.

When all of the above features are calculated from a short (seconds) Digital Record, the resulting feature values are called Snapshot Features. When all of the above features are calculated from a Snapshot Feature History File (hours/days/weeks), the resulting feature values are designated Trend Features.

Figure 13:
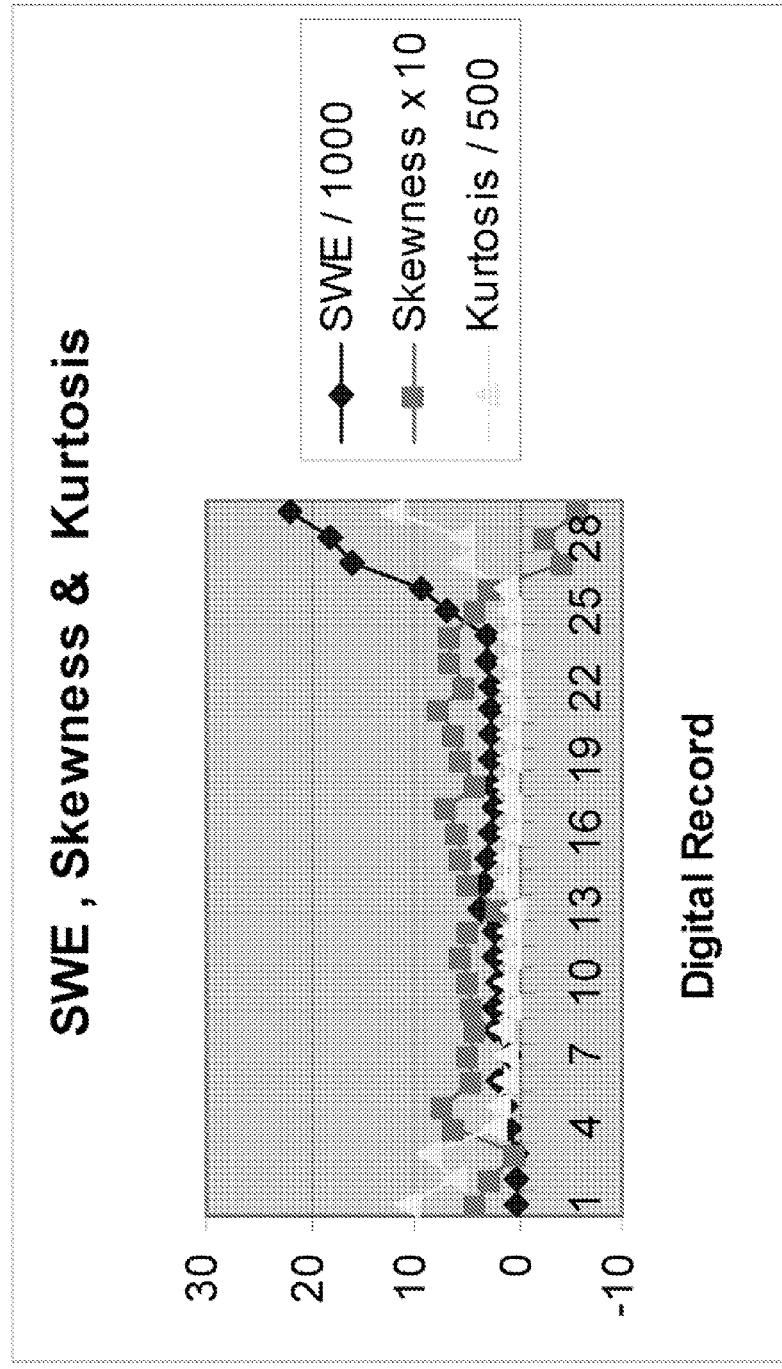
FIG. 13 provides an example plot used to illustrate the actual application of the statistical techniques discussed herein for monitoring the degradation and ultimate failure of a typical rolling element bearing.

FIG. 13 is an example (from an actual bearing failure) of how the PDF statistical descriptors of stress wave features can be employed to monitor the health and deterioration of a rolling element bearing.

The Delta Function

All of the above Snapshot and Trend features can be calculated from DR's acquired from a single sensor location. The measurements and features from that single sensor location would therefore include the effects of normal operational fluctuations in speed and load. To minimize the effects due to this range of operational influences, a "Delta Function" can be applied to data from a plurality of sensors on the same machine. For the example, two sensors are used that are placed at different locations.

For machines with mechanically linked shafts, gears, and bearings, The SWAN Time Domain Feature readings (Snapshot and Trend) from two sensor locations should have a consistent difference at a fixed operating condition, and should "trend together" for variable speed/load profiles. The arithmetic difference between 2 (contemporary) Time Domain Feature values, from two sensors on the same machine, is called the Delta Function.

The trend of the SWE Delta Function should not be erratic, and should stay consistently within a well defined range over a range of normal operating conditions, such as speeds and loads. In this manner, the SWE Delta Function eliminates "common mode noise" from the 2 sensors, and is highly coherent, under normal conditions with healthy mechanical components and effective lubrication. However, if a problem develops with a component that is closer to one sensor than the other, the Delta Function will change. Under these abnormal conditions, the Delta Function will become erratic and the nominal difference will increase. These changes in the Delta Function can be easily detected by the Time Domain Feature Extraction software, and (if desired) an associated Anomaly Detection Network (ADN).

The SAME Time Domain Feature Extraction software can be used to compute Delta Function "Snapshot" Features from 2 second DR's; as well as to compute Delta Function "Trend" Features from sets of historical data, that are hours or days long.]

This means that only one set of Trend Domain features needs to be calculated, and only one ADN needs to be developed/implemented/maintained, for a machine with 2 or more sensor locations.

The following Delta Function example was used for a large, main propulsion electric motor, such as those used on a cruise ship.

SWE from properly operating bearings on both ends of the same shaft, though different, should be strongly correlated (track up and down together) over a full range of operating loads and speeds. This is shown in FIG. 9A, where the delta functions of both sets of data tend to fall within a relatively narrow range, and thus show a good correlation.

Figure 9A:
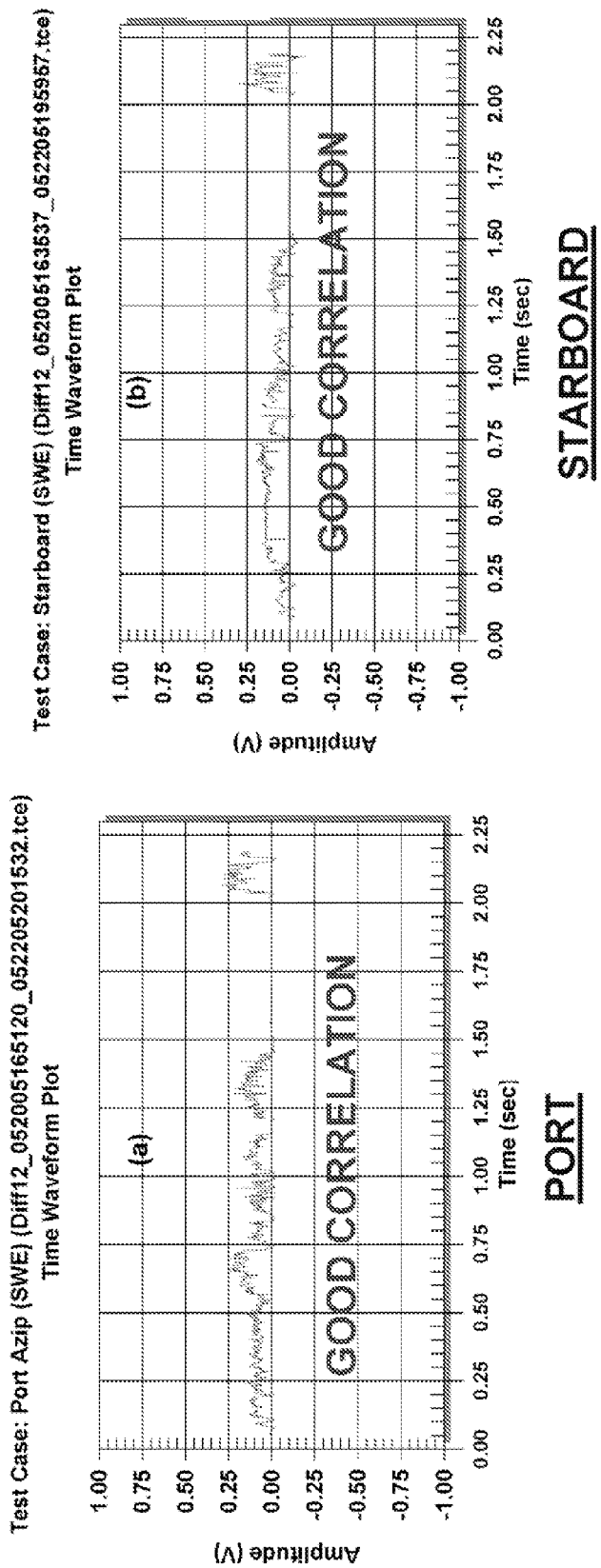
FIGS. 9A-9B graphically depict possible SWE Delta Function Histories for an example machine showing initial (FIG. 9A) and subsequent (FIG. 9B) readings.
Figure 9B:
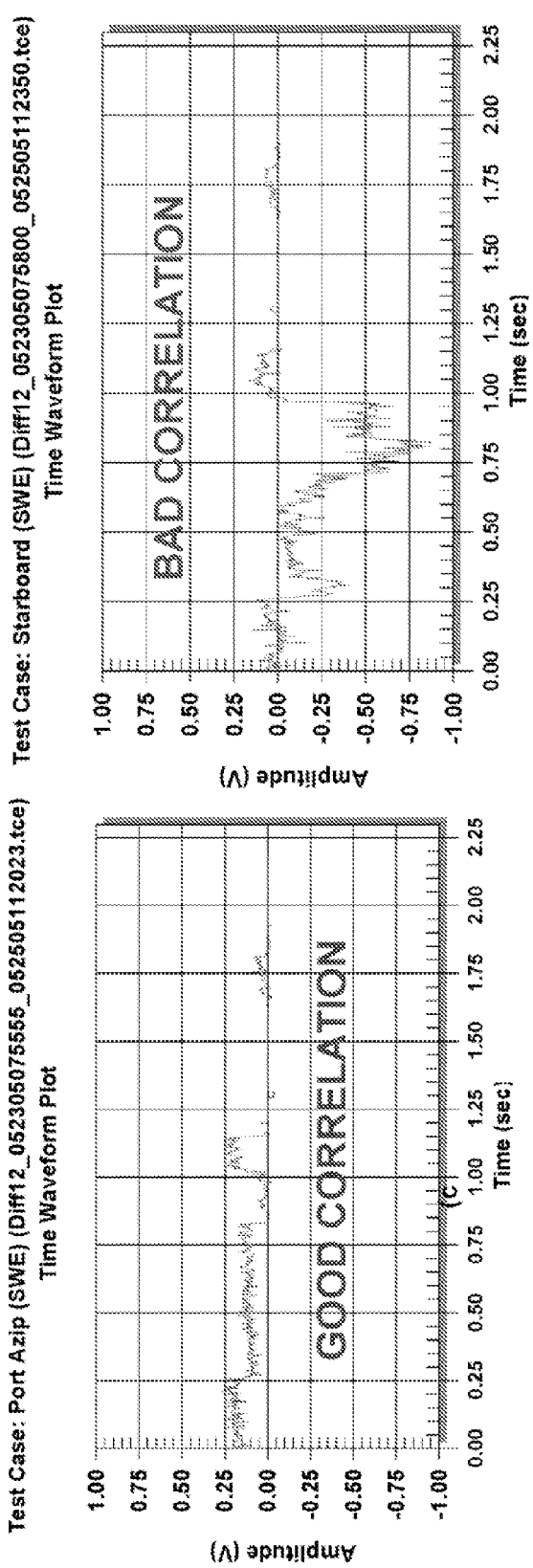

When something starts to go wrong, however, the correlation will change, as shown in FIG. 9B for the starboard readings. The change in correlation, due to some abnormal operation, will result in more "scatter" and an increased amount of difference between the SWE from the sensor at the good bearings and the sensor at the anomalous/discrepant bearings. The starboard sensors in the example of FIG. 9B are showing a divergence from the previously closely correlated values, thus implying a problem (or future potential problem) with the starboard engine.

In effect, the data plots in FIGS. 9A, 9B show the numerical difference between the SWE readings from the PROP end and THRUST end bearings of the port vs. starboard propulsion electric motors on the cruise ship. Each plot in these figures represents slightly more than 27 hours of elapsed time, and a full range of operating loads and speeds. It is apparent that the correlation between SWE readings from the PROP and THRUST ends of the port side motor is very good, and the DeltaSWE function varies in a tight range from −0.5 to +0.30 (see FIG. 9A).

However, the motor on the starboard side (operating over the same range of speeds and loads) begins to show a poor correlation between SWE readings from the PROP and THRUST end, as shown in FIG. 9B. The PDF that describes the statistical distribution of DeltaSWE readings will therefore be quite different for the two motors. In addition, whether the DeltaSWE PDF is positively or negatively skewed will indicate whether the discrepant condition is in the PROP or THRUST end of the motor.

Figure 10A:
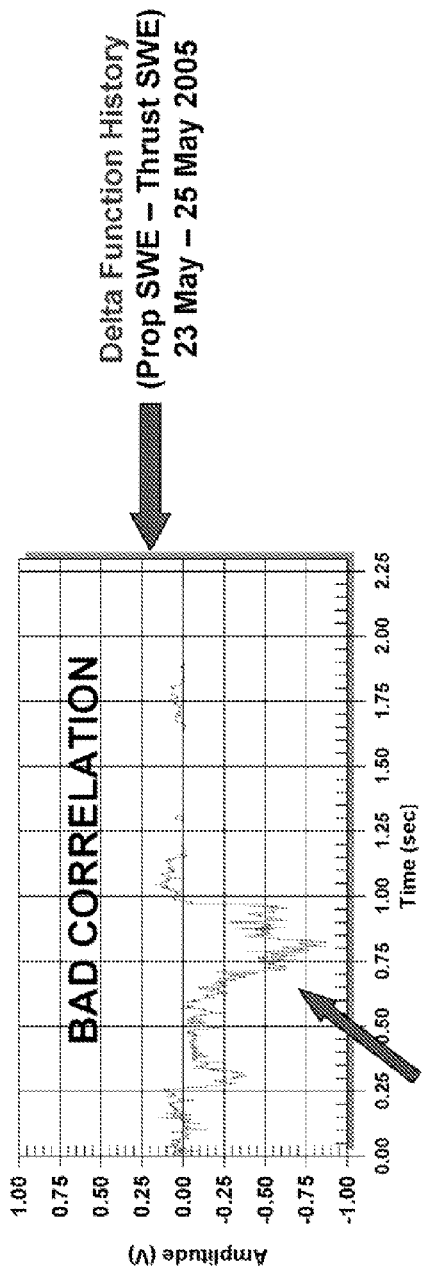
FIGS. 10A and 10B show a location of an abnormal event on example SWE Delta Function Histories as compared to the SWE readings.
Figure 10B:
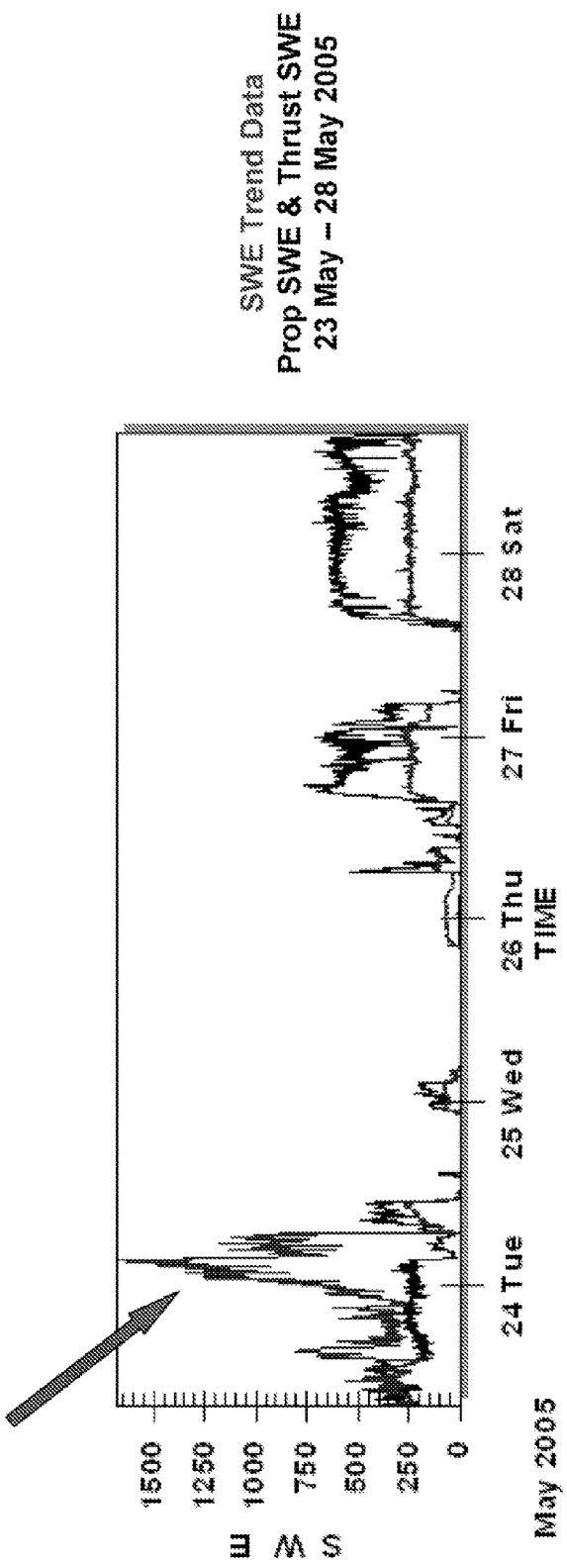

This Delta Function example was for a difference history of SWE snapshot readings, and FIGS. 10A and 10B show how the delta function correlates to the SWE trend data. The resulting features (obtained from application of TDFE software) are therefore Trend features. If the Delta Function calculation had been performed for the difference between "Window" SWE values within a pair of simultaneous 2 second digital records, the resulting feature would instead be a DeltaSWE/W Snapshot feature. Either can be utilized for the application discussed herein.

Figure 11A:
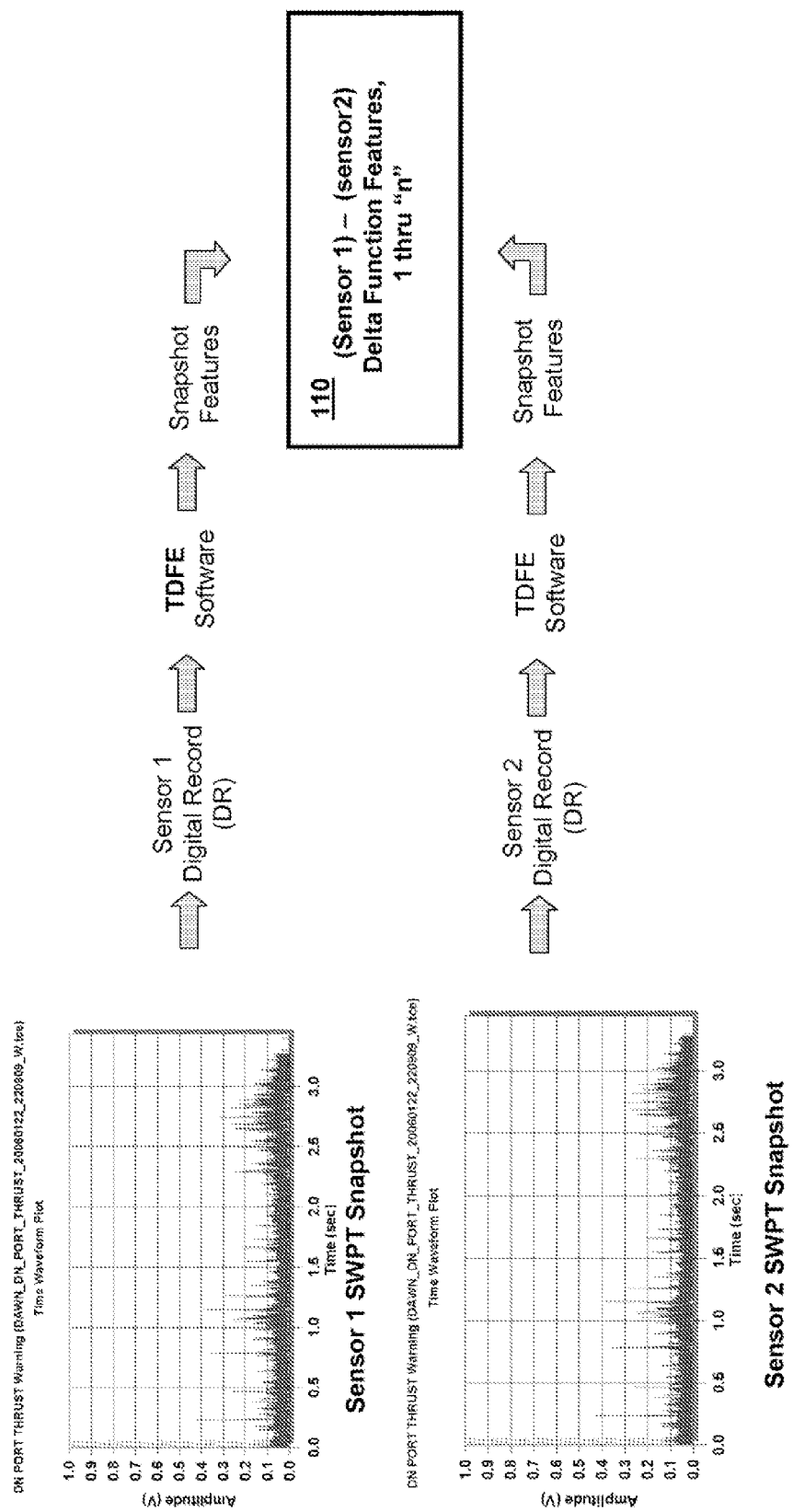
FIGS. 11A-11B are a block diagrams representing an example Delta Function Computational Process.
Figure 11B:
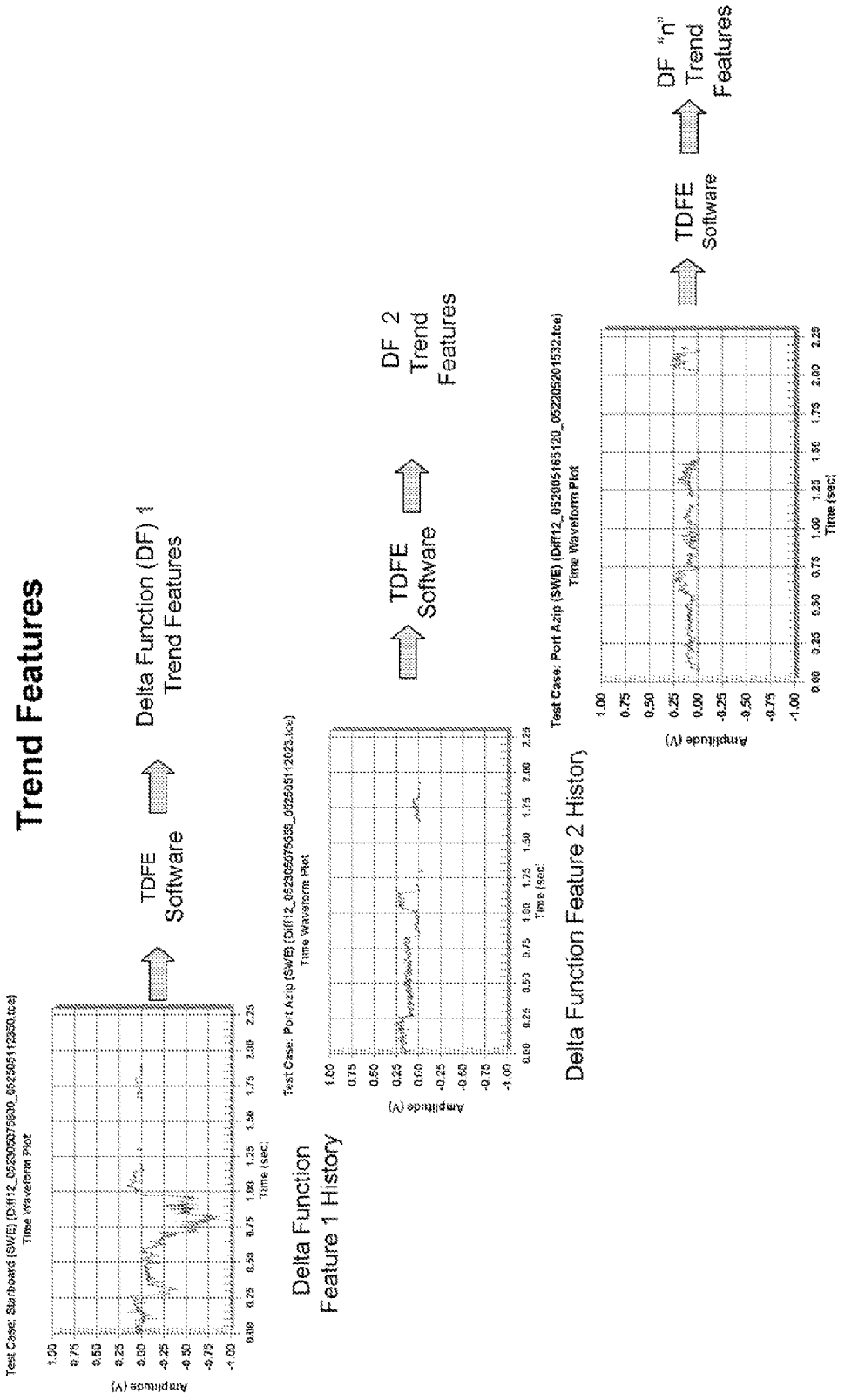

There are obviously a very large number of possible permutations and combinations for computing both Snapshot and Trend features. One example common process in application of the Delta Function is shown in FIGS. 11A and 11B, and include:

Acquire SWPT time waveform DR's from 2 simultaneously sampled sensors;
Apply TDFE software to each sensor's DR;
For each computed feature, calculate the difference between the Snapshot feature values for the two sensors (the Delta Function);
For each Delta Function feature, apply TDFE software to the Delta Function History, computed from a time series of DR pairs; and
Use the Delta Function Trend Features to characterize, and to classify, the Delta Function History time waveform.

The Cumulative (CUM) Function

The CUM function is applied to a History of Snapshot features, and can be used with a single sensor. It is therefore considered to be a Trend Feature. As its name implies, the CUM Function is the sum of all values, for a given snapshot feature, starting with the first value after a designated start point in time. The Snapshot features to which the CUM function is most commonly applied are SWE, Peak SWE, and Peak Duration.

The CUM function is employed to estimate "Life Used" or the probability of operating to a specified point, such as a warrantee period, without a failure. It can also be used, along with SWE level and rate of change, for making Remaining Useful Life Estimates (RULE's).

The following example shows how the CUM(SWE) function can be applied to estimate the probability that a gearbox will operate, without failure, throughout its 2 year warrantee period.

For a first step, assume as an example that 3 sensors are mounted on the subject gearbox, 6 months after the gearbox enters service. The first step is to perform a normal "first assessment" of the gearbox's health, utilizing previously described SWAN techniques. If the Unit Under Test (UUT) is not found to be healthy, data must be acquired from a like unit that is healthy and that operates under similar conditions. If the UUT is OK, then CUMSWE is calculated for a period of time (e.g., 1 month) that includes several cycles of operation over a full range of operating conditions.

The second step is to fit a curve to the 1 month of CUM (SWE) data points, and extrapolate it out, such as to the end of the warrantee period (another 17 months, in this example). The extrapolated value of CUM(SWE) at 24 months is the Normal Expected Value for CUM(SWE) at the end of the warrantee period. If the curve that best fits the trended CUM (SWE) data points is nonlinear, the best fit curve can be revised two or three or more times, on a periodic (e.g., monthly) basis, and new Normal Expected Values determined (assuming that the other SWAN results do not indicate a developing discrepant condition). If the CUM(SWE) trend is linear, these periodic revisions of the Normal Expected Value are not necessary.

The third step, in this example, is to fit a curve to the trend of CUM(SWE) data points, and extrapolate it out to the end of the warrantee period on a regular (e.g., weekly) basis. This periodic refit and extrapolation process is completed regardless of whether or not the other SWAN results indicate a developing discrepant condition, and produces a series of Actual Expected Values.

The final step is to compare the latest several Actual Expected Values to the Normal Expected Value (or range of Normal Expected Values, for machines with normal nonlinear wear out processes). If the Actual Expected Value persistently exceeds the Normal Expected Value, then the gearbox is unlikely to complete operating through its warrantee period, without developing a problem.

This process should be completed for each sensor on the gearbox, or for the Delta Functions between two or all three sensors.

Benefits and Features of Some Example Embodiments of the Invention

Experience and experiment have shown that the friction and shock parameters, as measured by SWAN, are the end results of a complex, nonlinear system of: mechanical elements, fluid dynamics, operating speeds, and dynamic loading. For this reason, SWAN data are more chaotic than deterministic, and best described by the statistical distribution of data rather than a single value such as an instantaneously measured value in a population.

Under stress, such complex (nonlinear) systems exhibit early changes in system behavior and condition, as changes in the Probability Density Function (statistical distribution) of measured stress wave parameters, particularly in the + or −3 sigma range.

Statistical measures of the Probability Density Function (PDF) of trended stress wave features, over a range of operating conditions, can be used to detect changes to system stress/health, without the need for "normalization" of stress wave time domain features (to account for changes due to known independent variables, such as load and speed).

One PDF statistical descriptor of SWAN data that has been shown effective in classifying machine health, and has been added to Time Domain Feature Extraction (TDFE) software, is the Kurtosis of the PDF.

A second PDF statistical descriptor of SWAN data, that has been shown effective in classifying machine health, and has been added to Time Domain Feature Extraction (TDFE) software, is the Skewness Coefficient of the PDF.

For machines with mechanically linked shafts, gears, and bearings, the SWE readings from 2 sensor locations can be combined, using an algorithm, labeled the Delta Function, to eliminate common mode noise and provide a real time stress indicator for machines with either steady state or variable speed/load profiles.

"Snapshot Features" including statistical descriptors of feature values, are useful in classifying the operating stresses, condition, and "health", of operating machinery. Snapshot Features are computed by applying Time Domain Feature Extraction software to a short (seconds) Digital Record of the Stress Wave Pulse Train, over a narrow range of reference operating conditions.

"Trend Features" including statistical descriptors of Trend Feature values, are useful in classifying the operating stresses, condition, and "health", of operating machinery. Trend Features are computed by applying Time Domain Feature Extraction software to a History file (hours/days/weeks) covering a broad range of operating conditions, for a given Snapshot Feature.

The Trend Domain Features, including statistical descriptors of Trend Feature values, can be employed by decision making software, such as neural networks or rule based logic, in a suitably configured Data Fusion Architecture (DFA) to classify machine health, over a broad range of operating conditions.

The CUM function can be employed to estimate "Life Used" or the probability of operating to a specified point, such as a warrantee period, without a failure. It can also be used, along with SWE level and rate of change, for making a Remaining Useful Life Estimate (RULE).

TABLE 1

Time Domain Features

| | Description | Notes |
|---|---|---|
| 1 | SWPD Stress Wave Peak Duration. The period of time between an upward a breech of the threshold L and when the Ai next falls below L. | Note that these features are calculated for each peak that occurs during an entire record (or history). |
| 2 | SWPA Stress Wave Peak Amplitude. The maximum value of Ai during the SWPD. | |
| 3 | SWPE Stress Wave Peak Energy. The sum of (Ai − L) for each data point during the SWPD. | |
| 4 | PADR Peak Amplitude to Duration Ratio. The ratio of SWPA to SWPD for an individual peak. | |
| 5 | SWE/W Stress Wave Energy per Window. The numeric sum of all the Ai values (greater than zero) for data points that occur during a window. | Note that these features are calculated for all the data points within each complete window, that fits within a Record (data from a fractional last window is dropped). |
| 6 | SWPE/W Stress Wave Peak Energy per Window. The sum of all the individual SWPE values within a window. | |
| 7 8 | PEF/W Peak Energy Factor per Window. The ratio of the SWPE/W to the SWE/W. PEAKS/W Peaks per Window. The total number of SWPT peaks that occur during an individual window. | |
| 9 | SWPD/W Stress Wave Peak Duration per Window. The sum of all SWPD values that occur within an individual window. | |
| 10 | WPAMR Window Peak Amplitude to Mean Ratio. The ratio of the maximum SWPA to the mean value of all data points, Ai, within an individual window. | |
| 11 | SWE/R Stress Wave Energy per Record. The numeric sum of all the Ai values greater than zero for all data points that occur during all windows of a data record. | Note that these features are calculated based upon the full record (or history) length |
| 12 | SWPE/R Stress Wave Peak Energy per Record. The sum of all the individual SWPE values within a record. | |
| 13 | PEAKS/R Peaks per Record. The total number of SWPT peaks that occur during a record. | |

TABLE 1-continued

Time Domain Features

| Description | Notes |
|---|---|
| 14 SWPA/R Stress Wave Peak Amplitude per Record. The maximum Ai value during the record. | |
| 15 PEF/R Peak Energy Factor per Record. The ratio of the SWPE/R to the SWE/R. | |
| 16 PAMR Peak Amplitude to Mean Ratio. The ratio of SWPA/R to the mean value of all data points, Ai, in the time record. | |
| 17 SWPD S1: 3rd Moment test for Normal Distribution. | Note that these features describe the Probability Density Function (PDF) of feature values for all the peaks in the record. |
| 18 SWPD S2: Maximum value of the population. | |
| 19 SWPD S3: The ratio of (Maximum − Mean)/(Maximum − Minimum) | |
| 20 SWPD S4: Ratio of the standard deviation of the population to the mean of the population. | |
| 21 SWPD S5: Skewness Coefficient. This is the ratio of S1 divided by the standard deviation. | |
| 22 SWPD S6: Kurtosis of the population. | |
| 23 SWPA S1: 3rd Moment test for Normal Distribution. | |
| 24 SWPA S2: Maximum value of the population. | |
| 25 SWPA S3: The ratio of (Maximum − Mean)/(Maximum − Minimum) | |
| 26 SWPA S4: Ratio of the standard deviation of the population to the mean of the population. | |
| 27 SWPA S5: Skewness Coefficient. This is the ratio of S1 divided by the standard deviation. | |
| 28 SWPA S6: Kurtosis of the population. | |
| 29 SWPE S1: 3rd Moment test for Normal Distribution. | |
| 30 SWPE S2: Maximum value of the population. | |
| 31 SWPE S3: The ratio of(Maximum − Mean)/(Maximum − Minimum) | |
| 32 SWPE S4: Ratio of the standard deviation of the population to the mean of the population. | |
| 33 SWPE S5: Skewness Coefficient. This is the ratio of S1 divided by the standard deviation. | |
| 34 SWPE S6: Kurtosis of the population. | |
| 35 PADR S1: 3rd Moment test for Normal Distribution. | |
| 36 PADR S2: Maximum value of the population. | |
| 37 PADR S3: The ratio of (Maximum − Mean)/(Maximum − Minimum) | |
| 38 PADR S4: Ratio of the standard deviation of the population to the mean of the population. | |
| 39 PADR S5: Skewness Coefficient. This is the ratio of S1 divided by the standard deviation. | |
| 40 PADR S6: Kurtosis of the population. | |
| 41 SWE/W S1: 3rd Moment test for Normal Distribution. | Note that these features describe the Probability Density Function (PDF) of feature values for all the complete windows in the record |
| 42 SWE/W S2: Maximum value of the population. | |
| 43 SWE/W S3: The ratio of (Maximum − Mean)/(Maximum − Minimum) | |
| 44 SWE/W S4: Ratio of the standard deviation of the population to the mean of the population. | |
| 45 SWE/W S5: Skewness Coefficient. This is the ratio of S1 divided by the standard deviation. | |
| 46 SWE/W S6: Kurtosis of the population. | |
| 47 SWPE/W S1: 3rd Moment test for Normal Distribution. | |
| 48 SWPE/W S2: Maximum value of the population. | |
| 49 SWPE/W S3: The ratio of (Maximum − Mean)/(Maximum − Minimum) | |
| 50 SWPE/W S4: Ratio of the standard deviation of the population to the mean of the population. | |
| 51 SWPE/W S5: Skewness Coefficient. This is the ratio of S1 divided by the standard deviation. | |
| 52 SWPE/W S6: Kurtosis of the population. | |
| 53 PEF/W S1: 3rd Moment test for Normal Distribution. | |
| 54 PEF/W S2: Maximum value of the population. | |
| 55 PEF/W S3: The ratio of (Maximum − Mean)/(Maximum − Minimum) | |
| 56 PEF/W S4: Ratio of the standard deviation of the population to the mean of the population. | |
| 57 PEF/W S5: Skewness Coefficient. This is the ratio of S1 divided by the standard deviation. | |
| 58 PEAKS/W S6: Kurtosis of the population. | |
| 59 PEAKS/W S1: 3rd Moment test for Normal Distribution. | |
| 60 PEAKS/W S2: Maximum value of the population. | |
| 61 PEAKS/W S3: The ratio of (Maximum − Mean)/(Maximum − Minimum) | |

TABLE 1-continued

Time Domain Features

| Description | Notes |
|---|---|
| 62 PEAKS/W S4: Ratio of the standard deviation of the population to the mean of the population. | |
| 63 PEAKS/W S5: Skewness Coefficient. This is the ratio of S1 divided by the standard deviation. | |
| 64 PEAKS/W S6: Kurtosis of the population. | |
| 65 SWPD/W S1: 3rd Moment test for Normal Distribution. | |
| 66 SWPD/W S2: Maximum value of the population. | |
| 67 SWPD/W S3: The ratio of (Maximum − Mean)/(Maximum − Minimum) | |
| 68 SWPD/W S4: Ratio of the standard deviation of the population to the mean of the population. | |
| 69 SWPD/W S5: Skewness Coefficient. This is the ratio of S1 divided by the standard deviation. | |
| 70 SWPD/W S6: Kurtosis of the population. | |
| 71 WPAMR/W S1: 3rd Moment test for Normal Distribution. | |
| 72 WPAMR/W S2: Maximum value of the population. | |
| 73 WPAMR/W S3: The ratio of (Maximum − Mean)/(Maximum − Minimum) | |
| 74 WPAMR/W S4: Ratio of the standard deviation of the population to the mean of the population. | |
| 75 WPAMR/W S5: Skewness Coefficient. This is the ratio of S1 divided by the standard deviation. | |
| 76 WPAMR/W S6: Kurtosis of the population. | |

Figure 12:
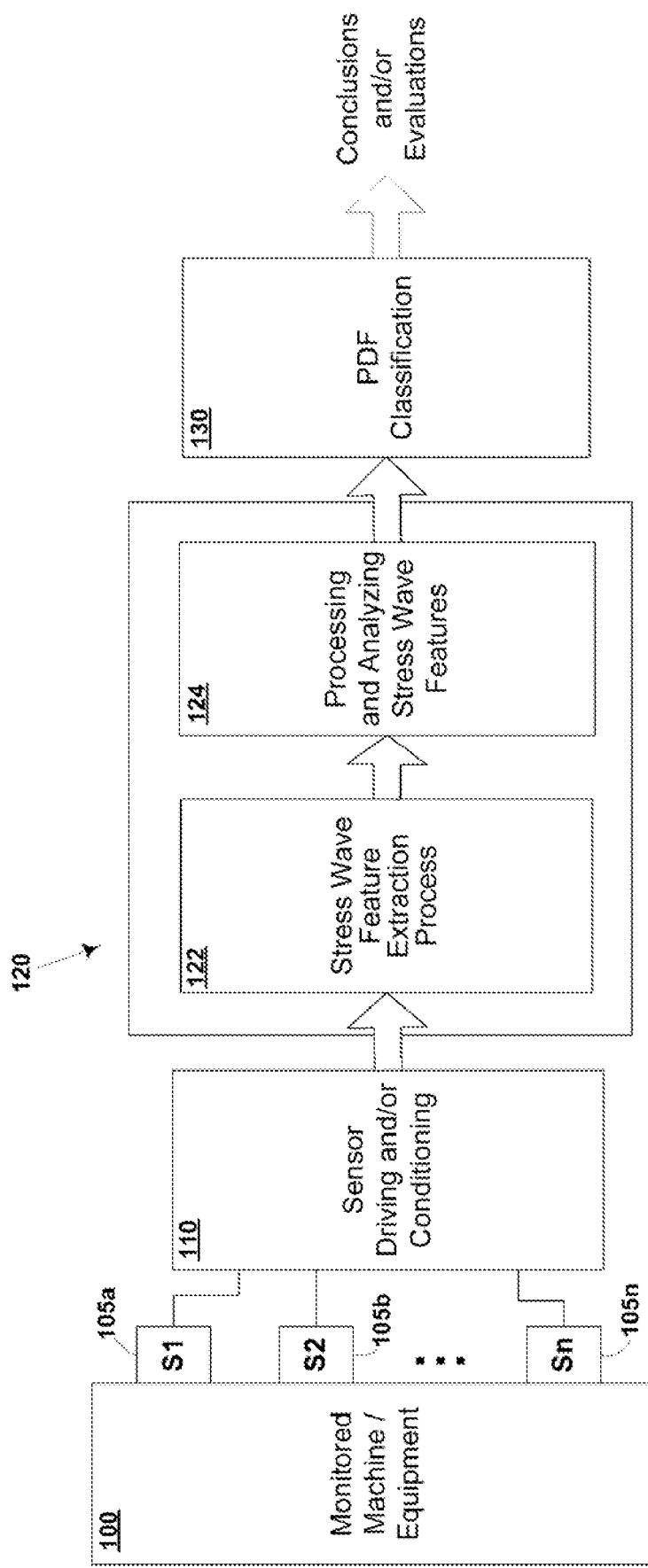
FIG. 12 is a simplified functional block diagram representing an example system for utilizing the probabilistic and/or delta function analysis methods described herein.

FIG. 12 shows an example system for implementing the techniques identified herein. The monitored machine/equipment 100 has one or more sensors S1, S2 . . . Sn mounted thereon or therein (105a, 105b . . . 105n, respectively). The sensors may need to be driven and/or their outputs conditioned by a driving/conditioning circuit 110. The output of the circuit 110 feeds a process 122 for extracting stress wave features (examples of which are discussed in the incorporated patent disclosures), which then feeds a process 124 for performing the trending and/or difference calculations that are utilized to monitor the status of the machine/equipment 100. This process could be implemented by one or more processors, such as a general purpose CPU, for example. Then, the output of the trending and/or difference calculations are compared, either automatically, for example by using a PDF Classification process 130 (and/or comparing to predetermined baselines), or manually, and a determination is output as to whether there is a problem with the machine/equipment 100.

The processes 122, 124 would typically be implemented on a common processor 120 (such as a CPU or dedicated controller), but different processors could be utilized for each process, if desired. Processors utilized by the monitored apparatus/equipment might also be utilized for performing these processing functions, or remote computing might be utilized. In addition, process 130 could be implemented on processor 120, or a different processor such as one of those described above. Clearly, these processor(s) would be executing programs to implement the described methods in any of the manners known in the art, or to be developed in the future.

Provided below is a description of the various statistical parameters that can be utilized to evaluate the monitored systems:

Statistical measures of the Probability Density Function (PDF) of trended stress wave features, over a range of operating conditions, can be used to detect changes to system stress/health, without the need for "normalization" of stress wave time domain features (e.g., to account for changes due to known independent variables, such as load and speed).

One PDF statistical descriptor of SWAN data that has been shown effective in classifying machine health, and has been added to Time Domain Feature Extraction (TDFE) software, is the Kurtosis of the PDF.

A second PDF statistical descriptor of SWAN data, that has been shown effective in classifying machine health, and has been added to Time Domain Feature Extraction (TDFE) software, is the Skewness Coefficient of the PDF.

For machines with mechanically linked shafts, gears, and bearings, the SWE readings from 2 sensor locations can be combined, using an algorithm, labeled the Delta Function, to eliminate common mode noise and provide a real time stress indicator for machines with either steady state or variable speed/load profiles.

"Trend Features" including statistical descriptors of Trend Feature values, are useful in classifying the operating stresses, condition, and "health", of operating machinery. Trend Features are computed by applying Time Domain Feature Extraction software to a History file (hours/days/weeks) covering a broad range of operating conditions, for a given Snapshot Feature.

The Trend Domain Features, including statistical descriptors of Trend Feature values, can be employed by decision making software, such as neural networks or rule based logic, in a suitably configured Data Fusion Architecture (DFA) to classify machine health, over a broad range of operating conditions.

The CUM function can be employed to estimate "Life Used" or the probability of operating to a specified point, such as a warrantee period, without a failure. It can also be used, along with SWE level and rate of change, for making a Remaining Useful Life Estimate (RULE).

Again, FIG. 13 provides an example plot used to illustrate the actual application of PSWAN statistical techniques to monitoring the degradation and ultimate failure of a typical rolling element bearing. The figure shows the combined trends of SWE, skewness, and kurtosis that can be utilized to provide unambiguous indications of:

The onset of fatigue damage to bearing contact surfaces, during the early stages of the failure process;

The progression of damage, during the early and mid stages of the failure process; and The increasing rate and amount of damage, late in the failure process, but prior to imminent failure.

Finally, although the examples given above utilize the disclosed methods and features as applied primarily to a single specific machine, the techniques disclosed herein may also be applied to a population of similar machines to develop a generic PDF that describes normal healthy operation in those machines, and then used to compare the PDF evolution of a single machine to that of the generic "baseline" PDF. Hence, the techniques can be generalized to a series of similar machines (e.g., a manufacturing line), rather than being adapted for the specific machine that is going to be monitored. If necessary, adjustments could be made to the models based on any unique characteristics that might develop for the specific machine being monitored in a given application, whether those characteristics are due to application or the idiosyncrasies of that particular machine.

The invention has been described hereinabove using specific examples and embodiments; however, it will be understood by those skilled in the art that various alternatives may be used and equivalents may be substituted for elements and/or steps described herein, without deviating from the scope of the invention. Modifications may be necessary to adapt the invention to a particular situation or to particular needs without departing from the scope of the invention. It is intended that the invention not be limited to the particular implementations and embodiments described herein, but that the claims be given their broadest interpretation to cover all embodiments, literal or equivalent, disclosed or not, covered thereby.

What is claimed is:

1. A method for determining a current status of an apparatus, said method comprising the steps of:

monitoring stress waves generated by the apparatus during a normal operation of the apparatus for at least one time period to generate first stress wave data;

analyzing at least a portion of said first stress wave data to generate first analyzed data that captures one or more features of said first stress wave data;

processing at least a portion of said first analyzed data to generate baseline data, wherein said baseline data has substantially reduced influence from normal operating variations compared to said first analyzed data;

further monitoring stress waves generated by the apparatus during a current operation of the apparatus for a current time period to generate second stress wave data;

analyzing at least a portion of said second stress wave data to generate second analyzed data that captures one or more features of said second stress wave data;

processing at least a portion of said second analyzed data to generate current status data, wherein said current status data also has substantially reduced influence from normal operating variations compared to said second analyzed data; and comparing said current status data to said baseline data to determine the current status of the apparatus.

2. The method of claim 1, wherein said baseline data includes baseline probabilistic data representing a normal operating condition of the apparatus, and wherein said current status data includes current probabilistic data representing a current operating condition, and further wherein said comparing step compares said baseline probabilistic data to said current probabilistic data to determine said current status of the apparatus.

3. The method of claim 2, wherein both of said probabilistic data includes statistical measures of the Probability Density Function of the corresponding source data.

4. The method of claim 2, wherein both of said probabilistic data include the results of one or more of: a third moment test for a normal distribution, a maximum value of the population, a ratio of (the maximum the mean) divided by (the maximum–the minimum), a ratio of the standard deviation of the population to the mean of the population, a skewness coefficient, and the kurtosis of the population.

5. The method of claim 4, wherein said comparing step examines a distortion of the probabilistic data of said current status data as compared to the probabilistic data of said baseline data to determine if a failure or a deterioration of the apparatus currently exists, or is likely to occur at some point in the future.

6. The method of claim 1, wherein said first stress wave data includes data obtained from a first location of the apparatus, and also includes data obtained from a second location of the apparatus different from said first location.

7. The method of claim 6, wherein said baseline data is derived from a difference between the portion of said first analyzed data obtained from said first location and the portion of said first analyzed data obtained from said second location.

8. The method of claim 6, wherein said second stress wave data includes data obtained from said first location of the apparatus, and also includes data obtained from said second location of the apparatus.

9. The method of claim 8, wherein said baseline data is derived from a difference between the portion of said first analyzed data obtained from said first location and the portion of said first analyzed data obtained from said second location, and further wherein said current status data is derived from a difference between the portion of said second analyzed data obtained from said first location and the portion of said second analyzed data obtained from said second location.

10. The method of claim 9, wherein said baseline data provides a normal operating threshold of the apparatus, and wherein, when said comparing of said current status data to said baseline data results in said current status data falling outside of said normal operating threshold, it is determined that a failure or a deterioration of the apparatus currently exists, or is likely to occur at some point in the future.

11. A method for determining a current status of an apparatus, said method comprising the steps of:

monitoring stress waves generated by the apparatus during a current operation of the apparatus for a current time period to generate current stress wave data;

analyzing at least a portion of said current stress wave data to generate current analyzed data that captures one or more features of said current stress wave data;

processing at least a portion of said current analyzed data to generate probabilistic current status data, wherein said probabilistic current status data has substantially reduced influence from normal operating variations compared to said current analyzed data; and comparing said probabilistic current status data to probabilistic baseline data to determine the current status of the apparatus.

12. The method of claim 11, wherein both of said probabilistic data includes statistical measures of the Probability Density Function of the corresponding source data.

13. The method of claim 11, further comprising the step of determining said probabilistic baseline data by a method including the steps of:
    monitoring stress waves generated by the apparatus during a normal operation of the apparatus for a plurality of time periods to generate a baseline series of stress wave data;
    analyzing at least a portion of said baseline series of stress wave data to generate a baseline series of analyzed data that captures one or more features of said baseline series of stress wave data; and
    processing at least a portion of said baseline series of analyzed data to generate said probabilistic baseline data.

14. The method of claim 13, wherein both of said probabilistic baseline data and said probabilistic current status data include the results of one or more of: a third moment test for a normal distribution, a maximum value of the population, a ratio of (the maximum−the mean) divided by (the maximum−the minimum), a ratio of the standard deviation of the population to the mean of the population, a skewness coefficient, and the kurtosis of the population.

15. The method of claim 14, wherein said comparing step examines a distortion of the said probabilistic current status data as compared to said probabilistic baseline data to determine if a failure or a deterioration of the apparatus currently exists, or is likely to occur at some point in the future.

16. The method of claim 11, wherein said probabilistic current status data include the results of one or more of: a third moment test for a normal distribution, a maximum value of the population, a ratio of (the maximum−the mean) divided by (the maximum−the minimum), a ratio of the standard deviation of the population to the mean of the population, a skewness coefficient, and the kurtosis of the population.

17. The method of claim 11, wherein said comparing step examines a distortion of the said probabilistic current status data as compared to said probabilistic baseline data to determine if a failure or a deterioration of the apparatus currently exists, or is likely to occur at some point in the future.

18. A method for determining a current status of an apparatus, said method comprising the steps of:
    monitoring stress waves generated by the apparatus at a first location during a current operation of the apparatus for a current time period to generate first current stress wave data;
    analyzing at least a portion of said first current stress wave data to generate first current analyzed data that captures one or more features of said first current stress wave data;
    monitoring stress waves generated by the apparatus at a second location different than said first location during the current operation of the apparatus for said current time period to generate second current stress wave data;
    analyzing at least a portion of said second current stress wave data to generate second current analyzed data that captures one or more features of said current second stress wave data;
    processing at least a portion of said first current analyzed data and said second current analyzed data to generate current status data based on a difference between said first current analyzed data and said second current analyzed data; and
    comparing said current status data to a threshold to determine the current status of the apparatus.

19. The method of claim 18, further comprising the step of determining said threshold by a method including the steps of:
    monitoring stress waves generated by the apparatus at said first location during a normal operation of the apparatus for at least one time period to generate first initial stress wave data;
    analyzing at least a portion of said first initial stress wave data to generate first initial analyzed data that captures one or more features of said first initial stress wave data;
    monitoring stress waves generated by the apparatus at said second location during the normal operation of the apparatus for said at least one time period to generate second initial stress wave data;
    analyzing at least a portion of said second initial stress wave data to generate second initial analyzed data that captures one or more features of said initial second stress wave data; and
    processing at least a portion of said first initial analyzed data and said second initial analyzed data to generate said threshold.

20. The method of claim 19, wherein said threshold is based on a difference between said first initial analyzed data and said second initial analyzed data.

21. The method of claim 19, said comparing is for determining if a failure or a deterioration of the apparatus currently exists, or is likely to occur at some point in the future.

22. The method of claim 18, wherein said threshold includes baseline PDF descriptors, and wherein said current status data includes current PDF descriptors such that said comparing includes comparing said current PDE descriptors to said baseline PDF descriptors.

23. A system for determining a current status of an apparatus, said system comprising:
    at least one sensor mounted on or in the apparatus for monitoring stress waves generated by the apparatus during a normal operation of the apparatus for at least one time period to generate first stress wave data;
    a feature extraction device adapted for analyzing at least a portion of said first stress wave data to generate first analyzed data that captures one or more features of said first stress wave data;
    means for processing at least a portion of said first analyzed data to generate baseline data, wherein said baseline data has substantially reduced influence from normal operating variations compared to said first analyzed data;
    means for further monitoring stress waves generated by the apparatus during a current operation of the apparatus for a current time period to generate second stress wave data, wherein said means for further monitoring includes one or both of: said at least one sensor, and/or another sensor mounted on or in the apparatus;
    means for analyzing at least a portion of said second stress wave data to generate second analyzed data that captures one or more features of said second stress wave data;
    means for processing at least a portion of said second analyzed data to generate current status data, wherein said current status data also has substantially reduced influence from normal operating variations compared to said second analyzed data; and
    means comparing said current status data to said baseline data to determine the current status of the apparatus.

24. The system of claim 23, wherein said baseline data includes baseline probabilistic data representing a normal operating condition of the apparatus, and wherein said current status data includes current probabilistic data representing a current operating condition, and further wherein said comparing step compares said baseline probabilistic data to said current probabilistic data to determine said current status of the apparatus.

25. The system of claim 24, wherein both of said probabilistic data includes statistical measures of the Probability Density Function of the corresponding source data.

26. The system of claim 24, wherein both of said probabilistic data include the results of one or more of: a third moment test for a normal distribution, a maximum value of the population, a ratio of (the maximum−the mean) divided by (the maximum−the minimum), a ratio of the standard deviation of the population to the mean of the population, a skewness coefficient, and the kurtosis of the population.

27. The system of claim 26, wherein said comparing step examines a distortion of the probabilistic data of said current status data as compared to the probabilistic data of said baseline data to determine if a failure or a deterioration of the apparatus currently exists, or is likely to occur at some point in the future.

28. The system of claim 23, said system further comprising at least one other sensor mounted in or on the apparatus at another location, wherein said first stress wave data includes data obtained from said at least one sensor and also data obtained from said at least one other sensor.

29. The system of claim 28, wherein said baseline data is derived from a difference between the data obtained from said at least one sensor and the data obtained from said at least one other sensor.

30. The system of claim 28, wherein said second stress wave data includes data obtained from said at least one sensor, and also includes data obtained from said at least one other sensor.

31. The system of claim 30, wherein
said baseline data is derived from a difference between the portion of said first analyzed data obtained from said at least one sensor and the portion of said first analyzed data obtained from said at least one other sensor, and further wherein
said current status data is derived from a difference between the portion of said second analyzed data obtained from said at least one sensor and the portion of said second analyzed data obtained from said at least one other sensor.

32. The system of claim 31 wherein said baseline data provides a normal operating threshold of the apparatus, and wherein, when said comparing of said current status data to said baseline data results in said current status data falling outside of said normal operating threshold, said system determines that a failure or a deterioration of the apparatus currently exists, or is likely to occur at some point in the future.

33. A system for determining a current status of an apparatus, said system comprising:
a sensor mounted on or in the apparatus for monitoring stress waves generated by the apparatus during a current operation of the apparatus for a current time period to generate current stress wave data;
means for analyzing at least a portion of said current stress wave data to generate current analyzed data that captures one or more features of said current stress wave data;
means for processing at least a portion of said current analyzed data to generate probabilistic current status data, wherein said probabilistic current status data has substantially reduced influence from normal operating variations compared to said current analyzed data; and
means for comparing said probabilistic current status data to probabilistic baseline data to determine the current status of the apparatus.

34. A system for determining a current status of an apparatus, said system comprising:
a first sensor mounted on or in the apparatus at a first location for monitoring stress waves generated by the apparatus during a current operation of the apparatus for a current time period to generate first current stress wave data;
means for analyzing at least a portion of said first current stress wave data to generate first current analyzed data that captures one or more features of said first current stress wave data;
a second sensor mounted on or in the apparatus at a second location different than said first location for monitoring stress waves generated by the apparatus during the current operation of the apparatus for said current time period to generate second current stress wave data;
means for analyzing at least a portion of said second current stress wave data to generate second current analyzed data that captures one or more features of said current second stress wave data;
means for processing at least a portion of said first current analyzed data and said second current analyzed data to generate current status data based on a difference between said first current analyzed data and said second current analyzed data; and
means for comparing said current status data to a threshold to determine the current status of the apparatus.

35. The system of claim 34, wherein said threshold includes baseline PDF descriptors, and wherein said current status data includes current PDF descriptors such that said means for comparing includes means for comparing said current PDF descriptors to said baseline PDF descriptors.

* * * * *